United States Patent
Wheldrake

(10) Patent No.: US 11,806,217 B2
(45) Date of Patent: Nov. 7, 2023

(54) WOUND DRESSING

(71) Applicant: Smith & Nephew PLC, Watford (GB)

(72) Inventor: Amy Nicole Wheldrake, East Yorkshire (GB)

(73) Assignee: Smith & Nephew PLC, Watford (GB)

( * ) Notice: Subject to any disclaimer, the term of this patent is extended or adjusted under 35 U.S.C. 154(b) by 850 days.

(21) Appl. No.: 16/468,602

(22) PCT Filed: Dec. 11, 2017

(86) PCT No.: PCT/EP2017/082167
§ 371 (c)(1),
(2) Date: Jun. 11, 2019

(87) PCT Pub. No.: WO2018/108784
PCT Pub. Date: Jun. 21, 2018

(65) Prior Publication Data
US 2020/0008981 A1    Jan. 9, 2020

(30) Foreign Application Priority Data

Dec. 12, 2016 (GB) .................... 1621057
Jun. 22, 2017 (GB) .................... 1709987

(51) Int. Cl.
*A61F 13/00* (2006.01)
*A61F 13/02* (2006.01)

(52) U.S. Cl.
CPC .... *A61F 13/0209* (2013.01); *A61F 13/00012* (2013.01); *A61F 13/00017* (2013.01); *A61F 13/00029* (2013.01); *A61F 13/00042* (2013.01); *A61F 13/00068* (2013.01)

(58) Field of Classification Search
CPC ............ A61F 13/0209; A61F 13/00012; A61F 13/00017; A61F 13/00029; A61F 13/00042; A61F 13/00068
See application file for complete search history.

(56) References Cited

U.S. PATENT DOCUMENTS

| | | |
|---|---|---|
| 3,441,023 A | 4/1969 | Rijssenbeek |
| 3,525,337 A | 8/1970 | Simons et al. |
| 3,972,328 A | 8/1976 | Chen |
| 4,029,598 A | 6/1977 | Neisius et al. |
| 4,578,070 A | 3/1986 | Holtman |
| 4,728,499 A | 3/1988 | Fehder |
| 4,813,942 A | 3/1989 | Alvarez |

(Continued)

FOREIGN PATENT DOCUMENTS

| | | |
|---|---|---|
| DE | 3443101 A1 | 5/1986 |
| EP | 0 321 980 | 6/1989 |

(Continued)

OTHER PUBLICATIONS

Great Britain Office Action and Search Report, re GB Application No. GB 1621057.7, dated Apr. 25, 2017.

(Continued)

*Primary Examiner* — Jessica Arble
(74) *Attorney, Agent, or Firm* — Knobbe, Martens, Olson & Bear, LLP

(57) ABSTRACT

The disclosed technology relates to a wound dressing comprising a vertically lapped material. The disclosed technology further relates to methods and uses of the wound dressing.

30 Claims, 15 Drawing Sheets

(56) References Cited

U.S. PATENT DOCUMENTS

| | | | |
|---|---|---|---|
| 4,927,685 A * | 5/1990 | Marshall | A61F 13/15658 604/374 |
| 5,056,510 A | 10/1991 | Gilman | |
| 5,149,332 A | 9/1992 | Walton et al. | |
| 5,167,654 A * | 12/1992 | Yang | A61F 5/4401 604/367 |
| 5,181,905 A | 1/1993 | Flam | |
| 5,238,732 A | 8/1993 | Krishnan | |
| 5,549,584 A | 8/1996 | Gross | |
| 5,707,499 A | 1/1998 | Joshi et al. | |
| 5,759,570 A | 6/1998 | Arnold | |
| 5,852,126 A | 12/1998 | Barnard et al. | |
| 6,071,267 A | 6/2000 | Zamierowski | |
| 6,626,891 B2 | 9/2003 | Ohmstede | |
| 6,673,982 B1 * | 1/2004 | Chen | A61F 13/53743 604/385.101 |
| 6,685,681 B2 | 2/2004 | Lockwood et al. | |
| 6,752,794 B2 | 6/2004 | Lockwood et al. | |
| 6,936,037 B2 | 8/2005 | Bubb et al. | |
| 6,951,553 B2 | 10/2005 | Bubb et al. | |
| 6,979,324 B2 | 12/2005 | Bybordi et al. | |
| 7,070,584 B2 | 7/2006 | Johnson et al. | |
| 7,108,683 B2 | 9/2006 | Zamierowski | |
| 7,216,651 B2 | 5/2007 | Argenta et al. | |
| 7,361,184 B2 | 4/2008 | Joshi | |
| 7,381,859 B2 | 6/2008 | Hunt et al. | |
| 7,605,298 B2 | 10/2009 | Bechert et al. | |
| 7,615,036 B2 | 11/2009 | Joshi et al. | |
| 7,622,629 B2 | 11/2009 | Aali | |
| 7,700,819 B2 | 4/2010 | Ambrosio et al. | |
| 7,708,724 B2 | 5/2010 | Weston | |
| 7,718,249 B2 | 5/2010 | Russell et al. | |
| 7,722,582 B2 | 5/2010 | Lina et al. | |
| 7,749,531 B2 | 7/2010 | Booher | |
| 7,759,537 B2 | 7/2010 | Bishop et al. | |
| 7,759,539 B2 | 7/2010 | Shaw et al. | |
| 7,775,998 B2 | 8/2010 | Riesinger | |
| 7,811,269 B2 | 10/2010 | Boynton et al. | |
| 7,910,791 B2 | 3/2011 | Coffey | |
| 7,922,703 B2 | 4/2011 | Riesinger | |
| 7,959,624 B2 | 6/2011 | Riesinger | |
| 7,976,519 B2 | 7/2011 | Bubb et al. | |
| 8,062,331 B2 | 11/2011 | Zamierowski | |
| 8,152,785 B2 | 4/2012 | Vitaris | |
| 8,162,907 B2 | 4/2012 | Heagle | |
| 8,235,972 B2 | 8/2012 | Adahan | |
| 8,241,261 B2 | 8/2012 | Randolph et al. | |
| 8,372,049 B2 | 2/2013 | Jaeb et al. | |
| 8,372,050 B2 | 2/2013 | Jaeb et al. | |
| 8,425,478 B2 | 4/2013 | Olson | |
| 8,513,481 B2 | 8/2013 | Gergely et al. | |
| 8,540,688 B2 | 9/2013 | Eckstein et al. | |
| 8,545,466 B2 | 10/2013 | Andresen et al. | |
| 8,568,386 B2 | 10/2013 | Malhi | |
| 8,628,505 B2 | 1/2014 | Weston | |
| 8,641,691 B2 | 2/2014 | Fink et al. | |
| 8,663,198 B2 | 3/2014 | Buan et al. | |
| 8,795,243 B2 | 8/2014 | Weston | |
| 8,795,800 B2 | 8/2014 | Evans | |
| 9,067,003 B2 | 6/2015 | Buan et al. | |
| 9,127,665 B2 | 9/2015 | Locke et al. | |
| 9,220,822 B2 | 12/2015 | Hartwell | |
| 9,283,118 B2 | 3/2016 | Locke et al. | |
| 9,302,033 B2 | 4/2016 | Riesinger | |
| 9,375,521 B2 | 6/2016 | Hudspeth et al. | |
| 9,381,283 B2 | 7/2016 | Adams et al. | |
| 9,421,309 B2 | 8/2016 | Robinson et al. | |
| 9,427,505 B2 | 8/2016 | Askem et al. | |
| 9,452,248 B2 | 9/2016 | Blott et al. | |
| 9,629,986 B2 | 4/2017 | Patel et al. | |
| 9,681,993 B2 | 6/2017 | Wu et al. | |
| 9,682,179 B2 | 6/2017 | May | |
| 9,795,725 B2 | 10/2017 | Joshi et al. | |
| 9,808,561 B2 | 11/2017 | Adie et al. | |
| 9,829,471 B2 | 11/2017 | Hammond et al. | |
| 9,844,473 B2 | 12/2017 | Blott et al. | |
| 9,962,474 B2 | 5/2018 | Greener | |
| 10,046,096 B2 | 8/2018 | Askem et al. | |
| 10,105,471 B2 | 10/2018 | Weston | |
| 10,188,555 B2 | 1/2019 | Vitaris et al. | |
| 10,328,188 B2 | 6/2019 | Deutsch et al. | |
| 10,493,184 B2 | 12/2019 | Collinson et al. | |
| 2003/0125646 A1 | 7/2003 | Whitlock | |
| 2004/0057855 A1 | 3/2004 | Gerlach et al. | |
| 2006/0009744 A1 | 1/2006 | Erdman et al. | |
| 2006/0025727 A1 | 2/2006 | Boehringer et al. | |
| 2007/0016152 A1 | 1/2007 | Karpowicz et al. | |
| 2007/0040454 A1 | 2/2007 | Freudenberger et al. | |
| 2007/0078366 A1 * | 4/2007 | Haggstrom | A61M 1/732 602/53 |
| 2007/0197988 A1 | 8/2007 | Bieling et al. | |
| 2007/0225663 A1 | 9/2007 | Watt et al. | |
| 2007/0255194 A1 | 11/2007 | Gudnason et al. | |
| 2008/0031748 A1 | 2/2008 | Ihle et al. | |
| 2008/0132821 A1 | 6/2008 | Propp et al. | |
| 2009/0062760 A1 * | 3/2009 | Wright | A61F 13/15747 604/378 |
| 2009/0125004 A1 | 5/2009 | Shen et al. | |
| 2009/0157024 A1 | 6/2009 | Song | |
| 2009/0234306 A1 | 9/2009 | Vitaris | |
| 2009/0299306 A1 | 12/2009 | Buan | |
| 2010/0036334 A1 * | 2/2010 | Heagle | A61M 1/982 604/319 |
| 2010/0125258 A1 | 5/2010 | Coulthard et al. | |
| 2010/0259406 A1 | 10/2010 | Caso et al. | |
| 2010/0318052 A1 | 12/2010 | Ha et al. | |
| 2011/0004172 A1 | 1/2011 | Eckstein et al. | |
| 2011/0224631 A1 | 9/2011 | Simmons et al. | |
| 2012/0051945 A1 | 3/2012 | Orndorff et al. | |
| 2013/0066285 A1 | 3/2013 | Locke et al. | |
| 2013/0066289 A1 | 3/2013 | Song et al. | |
| 2013/0090616 A1 | 4/2013 | Neubauer | |
| 2013/0138054 A1 | 5/2013 | Fleischmann | |
| 2013/0144227 A1 | 6/2013 | Locke et al. | |
| 2013/0165878 A1 | 6/2013 | Heagle | |
| 2013/0296762 A1 | 11/2013 | Toth | |
| 2013/0302545 A1 | 11/2013 | Schnelker et al. | |
| 2014/0114268 A1 | 4/2014 | Auguste et al. | |
| 2014/0200533 A1 | 7/2014 | Whyte et al. | |
| 2014/0316359 A1 | 10/2014 | Collinson et al. | |
| 2014/0330224 A1 * | 11/2014 | Albert | A61F 13/02 604/319 |
| 2015/0032035 A1 | 1/2015 | Banwell et al. | |
| 2015/0119831 A1 | 4/2015 | Robinson et al. | |
| 2015/0119832 A1 | 4/2015 | Locke | |
| 2015/0119833 A1 | 4/2015 | Coulthard et al. | |
| 2015/0148760 A1 | 5/2015 | Dodd et al. | |
| 2015/0216733 A1 * | 8/2015 | Allen | A61F 13/0216 604/319 |
| 2016/0000611 A1 | 1/2016 | Niederauer et al. | |
| 2016/0298620 A1 | 10/2016 | Cordoba et al. | |
| 2017/0128642 A1 | 5/2017 | Buan | |
| 2017/0181896 A1 | 6/2017 | Hartwell | |
| 2017/0368239 A1 | 12/2017 | Askem et al. | |
| 2018/0133378 A1 | 5/2018 | Askem et al. | |
| 2018/0318476 A1 | 11/2018 | Askem et al. | |
| 2020/0121833 A9 | 4/2020 | Askem et al. | |
| 2020/0139023 A1 | 5/2020 | Haggstrom et al. | |

FOREIGN PATENT DOCUMENTS

| | | |
|---|---|---|
| EP | 0340018 A2 | 11/1989 |
| EP | 0 752 839 | 5/1998 |
| EP | 1476217 B1 | 3/2008 |
| EP | 1955887 A2 | 8/2008 |
| EP | 2462908 A1 | 6/2012 |
| EP | 3628289 B1 | 11/2021 |
| FR | 1163907 A | 10/1958 |
| FR | 2 146 127 | 3/1973 |
| FR | 2 504 799 | 11/1982 |
| GB | 1255395 A | 12/1971 |
| GB | 1312370 | 4/1973 |
| GB | 2307180 B | 6/2000 |

(56) References Cited

FOREIGN PATENT DOCUMENTS

| | | |
|---|---|---|
| GB | 2468905 A | 9/2010 |
| WO | WO-8300742 A1 | 3/1983 |
| WO | WO-9216245 A1 | 10/1992 |
| WO | WO-9605873 A1 | 2/1996 |
| WO | WO 2000/036199 | 6/2000 |
| WO | WO 2002/034188 | 5/2002 |
| WO | WO-2004077387 A1 | 9/2004 |
| WO | WO-2005046760 A1 | 5/2005 |
| WO | WO-2005105180 A1 | 11/2005 |
| WO | WO-2007113597 A2 | 10/2007 |
| WO | WO-2008039223 A1 | 4/2008 |
| WO | WO-2009124100 A1 | 10/2009 |
| WO | WO-2009147402 A2 | 12/2009 |
| WO | WO-2009158128 A2 | 12/2009 |
| WO | WO-2010142959 A2 | 12/2010 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO 2012/057881 | 5/2012 |
| WO | WO 2012/125530 | 9/2012 |
| WO | WO-2012131237 A1 | 10/2012 |
| WO | WO-2012143665 A1 | 10/2012 |
| WO | WO-2013010907 A1 | 1/2013 |
| WO | WO-2013064852 A1 | 5/2013 |
| WO | WO-2013083800 A1 | 6/2013 |
| WO | WO-2013090810 A1 | 6/2013 |
| WO | WO-2013149078 A1 | 10/2013 |
| WO | WO-2014008348 A2 | 1/2014 |
| WO | WO-2014016759 A1 | 1/2014 |
| WO | WO-2014020440 A1 | 2/2014 |
| WO | WO-2014108476 A1 | 7/2014 |
| WO | WO-2015022334 A1 | 2/2015 |
| WO | WO-2015022340 A1 | 2/2015 |
| WO | WO 2015/148636 | 10/2015 |
| WO | WO-2016018448 A1 | 2/2016 |
| WO | WO-2016174048 A1 | 11/2016 |
| WO | WO 2017/062309 | 4/2017 |
| WO | WO-2018164803 A1 | 9/2018 |

OTHER PUBLICATIONS

Great Britain Office Action and Search Report, re GB Application No. 1709987.0, dated Dec. 8, 2017.
International Search Report and Written Opinion, re PCT Application No. PCT/EP2017/082167, dated Jan. 25, 2018.
Advantec MFS, Inc., "Membrane Filters" (catalog), retrieved from http://www.advantecmfs.com/catalog/filt/membrane.pdf, on Jan. 29, 2016, Copyright 2001-2011, 17 pages.
Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.
International Preliminary Report on Patentability for Application No. PCT/EP2017/082167, dated Jun. 27, 2019, 12 pages.
Kendall ULTEC Hydrocolloid Dressing (4x4"), Product Ordering Page, web page downloaded on Jul. 13, 2014, 1 page.
Protz K., "Modern Wound Dressings Support the Healing Process," Wound care: Indications and Application, Geriatrie Journal, Apr. 2005, pp. 3333-3339 (17 pages with English translation).
Smith & Nephew, "PICO Single Use Negative Pressure Wound Therapy System," Spiral Booklet, Mar. 2011, 7 pages.
Technology Watch, May 1989, 1 page.

* cited by examiner

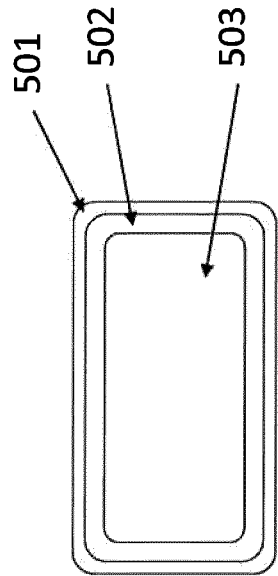
FIG. 5B
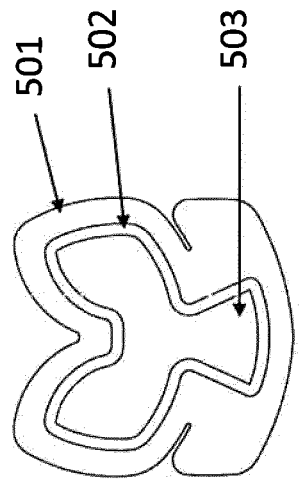
FIG. 5D
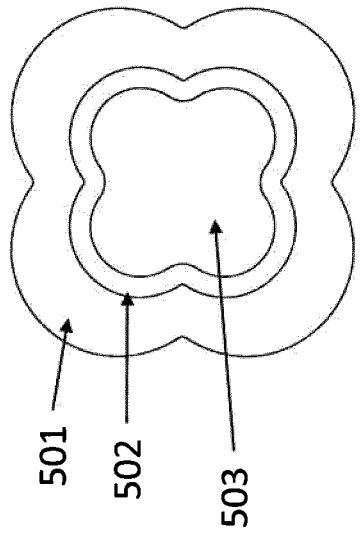
FIG. 5A
FIG. 5C

WOUND DRESSING

CROSS-REFERENCE TO RELATED APPLICATIONS

This application is a U.S. national stage application of International Patent Application No. PCT/EP2017/082167, filed Dec. 11, 2017, which claims the benefit of GB Application No. 1621057.7, filed Dec. 12, 2016, and GB Application No. 1709987.0, filed Jun. 22, 2017, the disclosure of each of which is hereby incorporated by reference in its entirety.

TECHNICAL FIELD

The disclosed technology relates to a wound dressing comprising a vertically lapped material. The disclosed technology further relates to methods and uses of the wound dressing.

BACKGROUND

In wound treatment there is a balance between providing a wound dressing to remove wound fluid which can accumulate between the dressing and the skin. A build up of fluid between the wound and the dressing can cause separation of the dressing from the skin. Separation of the dressing from the skin can increase the possibility of the wound being contaminated by microorganisms which can cause infection. However, the dressing should be in place for sufficient time to ensure the body can progress biological process required to heal a wound.

Depending on the nature of the wound, the patient may be immobilised for prolonged periods of time. Immobilisation of a patient or neuropathy may also lead to complicating factors such as ulcers (such as a pressure ulcer, or also known as a pressure injury) or bed sores.

Pressure ulcers (may be referred to as "bed sores" or decubitus ulcers) may be developed by individuals confined for an extended period of time to a particular position in a bed or chair. When a person is bed ridden or wheel chair bound due to such causes as an accident, illness, or extensive period of recovery from surgery, the body tends to be immobilized for an extended period of time. It has been noted that pressure ulcers occur most frequently in certain parts of the body, such as the heel and ankle, the trochanter, the sacrum, the scapulae, at the elbows, knees, occiput, ischial tuberosites and at the coccyx. As presently understood, the weight overlying these body parts exerts sufficient pressure on the underlying soft tissue layers to cause an interruption of the flow of blood to and through the soft tissue layers causing the development of a condition generally referred to as pressure ulcers.

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

SUMMARY

In one embodiment the disclosed technology relates to a wound dressing, and methods and uses of employing the wound dressing. Some embodiments may mitigate/reduce or prevent ulcer formation during wound healing. Some embodiments of the wound dressing may be adapted for use in negative pressure wound therapy.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the basic and novel characteristics of the composition, method or use under consideration.

In one embodiment the disclosed technology relates to a wound dressing comprising a vertically lapped material comprising:
    a first layer of an absorbing layer of material, and
    a second layer of material,
wherein the first layer being constructed from at least one layer of non-woven textile fibers, the non-woven textile fibers being folded into a plurality of folds to form a pleated structure; and
the second layer of material is temporarily or permanently connected to the first layer of material.

In one embodiment the disclosed technology relates to a wound dressing comprising a vertically lapped material comprising:
    a first layer of an absorbing layer of material, and
    a second layer of material,
wherein the first layer being constructed from at least one layer of non-woven textile fibers, the non-woven textile fibers being folded into a plurality of folds to form a pleated structure; and
the second layer of material is temporarily or permanently connected to the first layer of material, and
wherein the thickness of the wound dressing is between 1 and 20 mm (or 2 to 10, or 3 to 7 mm).

In one embodiment the disclosed technology relates to a wound dressing comprising a vertically lapped material comprising:
    a first layer of an absorbing layer of material, and
    a second layer of material, wherein the first layer being constructed from at least one layer of non-woven textile fibers, the non-woven textile fibers being folded into a plurality of folds to form a pleated structure, wherein a depth of the pleats of the pleated structure that has been slit determines a thickness of said first layer of material.

In one embodiment the disclosed technology relates to a wound dressing comprising a vertically lapped material comprising:
a first layer of an absorbing layer of material, and
a second layer of material,
wherein the first layer being constructed from at least one layer of non-woven textile fibers, the non-woven textile fibers being folded into a plurality of folds to form a pleated structure, wherein a depth of the pleats of the pleated structure that has been slit determines a thickness of said first layer of material; and wherein the thickness of the wound dressing is between 1 and 20 mm (or 2 to 10, or 3 to 7 mm).

In one embodiment the disclosed technology relates to a wound dressing comprising a vertically lapped material that has been slit comprising:
a first layer of an absorbing layer of material, and
a second layer of material,
wherein the first layer being constructed from at least one layer of non-woven textile fibers, the non-woven textile fibers being folded into a plurality of folds to form a pleated structure wherein a depth of the pleats of the pleated structure that has been slit determines a thickness of said first layer of material; and
the second layer of material is temporarily or permanently connected to the first layer of material.

In one embodiment the disclosed technology relates to a wound dressing comprising a vertically lapped material that has been slit comprising:
a first layer of an absorbing layer of material, and
a second layer of material,
wherein the first layer being constructed from at least one layer of non-woven textile fibers, the non-woven textile fibers being folded into a plurality of folds to form a pleated structure wherein a depth of the pleats of the pleated structure that has been slit determines a thickness of said first layer of material; and
the second layer of material is temporarily or permanently connected to the first layer of material, and wherein the thickness of the wound dressing is between 1 and 20 mm (or 2 to 10, or 3 to 7 mm).

In one embodiment the wound dressing disclosed herein, wherein the second layer may comprise of a single or multi-layer construction.

In one embodiment the wound dressing disclosed herein, wherein the second layer may comprise of a single or multi-layer construction, and the thickness of the wound dressing is between 1 and 20 mm (or 2 to 10, or 3 to 7 mm).

The wound dressing disclosed herein may be used as the dressing component of a negative pressure wound dressing apparatus in a dressing construction.

The wound dressing may be used as wound dressing for a non-negative pressure wound dressing apparatus.

The wound dressing may contain active ingredients such as silver, silver salts, iodine, charcoal or other components designed to provide antibacterial activity, odour control, debridement, proteolytic activity, biofilm disruptors or promote wound healing.

The wound dressing disclosed herein may be used on a variety of wounds of different sizes and wound types. For example, the wound dressing may be used for chronic and acute wounds, such as; burns, surgical wounds, and trauma wounds.

Typically the wound type may be an ulcer such as a pressure ulcer.

The size of the wound dressing will depend on the nature of the wound being treated.

In one embodiment the disclosed technology relates to a method of treating an exudating wound, which comprises covering the wound area and a peri-wound area with a wound dressing disclosed herein.

In one embodiment the disclosed technology relates to a method of treating a human and/or animal wound comprising placing a wound dressing disclosed herein over the wound, and fixing the wound dressing to the peri-wound or other non-wound contact area. The wound dressing may be fixed to the peri-wound or other non-wound contact area by a dressing fixative.

In one embodiment the disclosed technology relates to the use of the wound dressing disclosed herein for use in treating a chronic wound, typically a pressure ulcer.

In one embodiment the disclosed technology relates to the use of the vertically lapped material disclosed herein as the absorbing layer of a wound dressing. The absorbing layer may remove exudate from the wound.

In one embodiment the disclosed technology relates to the use of the wound dressing disclosed herein for use in treating a chronic wound, ulcer or burn.

In one embodiment the disclosed technology relates to the use of the wound dressing disclosed herein for use in treating or preventing a pressure ulcer.

In one embodiment the disclosed technology relates to the use of the vertically lapped material disclosed herein as the absorbing layer of a wound dressing as a partial or complete replacement or in addition to a foam layer.

In one embodiment the disclosed technology relates to the use of the wound dressing disclosed herein as the absorbing layer of a wound dressing for reducing pressure on a wound site.

In one embodiment the disclosed technology relates to the use of the wound dressing disclosed herein as the absorbing layer of a wound dressing for reducing pressure on a wound site and absorbing wound exudate from the wound.

In one embodiment the disclosed technology relates to a method of treating an exudating wound, which comprises covering the wound area and a peri-wound area with a dressing disclosed herein.

In one embodiment the disclosed technology relates to the use of a wound dressing comprising a vertically lapped material comprising:
a first layer of an absorbing layer of material, and
wherein the first layer being constructed from at least one layer of non-woven textile fibers, the non-woven textile fibers being folded into a plurality of folds to form a pleated structure of as a wound filler.

In one embodiment the dressing layer of non-woven textile fibers is a wound filler. The non-woven textile fibers may be used as a full or partial replacement for a gauze, foams, sponges, cotton wads or other fibrous materials. Gauze and other fibrous materials absorb fluids by capillary action. However, gauze and other fibrous materials have the disadvantage in that when new tissue is formed, in the process of healing, it engulfs the fibers of these materials and it is torn when the material is removed causing potential wound injury on removal.

In this embodiment the vertically lapped non-woven may not be attached to a second layer, rather the surface may be heat treated to provide a 'skinned' surface. The 'skinned' surface is a smoothed surface which may be achieved by heat treatment such as calendaring.

In one embodiment the vertically lapped non-woven is used as a wound filler as outlined above with or without negative pressure.

In some aspects, a wound dressing comprises at least one layer of a vertically lapped material and a cover layer configured to cover and form a seal over a wound, and wherein the at least one layer of the vertically lapped material being constructed from at least one layer of non-woven textile fibers, the non-woven textile fibers being folded into a plurality of folds to form a pleated structure.

The apparatus of the preceding paragraph may also include any combination of the following features described in this paragraph, among others described herein. The wound dressing can further comprise a wound contact layer. The at least one layer of the vertically lapped material can comprise an absorbent material configured to provide a reservoir for fluid removed from the wound. The wound dressing can further comprise a transmission layer configured to allows transmission of fluid away from a wound site into upper layers of the wound dressing. The at least one layer of the vertically lapped material can comprise a transmission layer configured to allows transmission of fluid away from a wound site into upper layers of the wound dressing. The wound dressing can further comprise an absorbent layer. The wound dressing can further comprise an obscuring layer. The obscuring layer can comprise one or more viewing windows. The at least one layer of the vertically lapped material can comprise an upper portion and a lower portion, wherein the upper portion and lower portion of the vertically lapped material are configured to be in fluid communication, the upper portion and lower portion are configured to allows transmission of fluid away from a wound site; and the wound dressing further comprises an absorbent layer, wherein the at least one layer of the vertically lapped material is configured to be wrapped around at least one edge of the absorbent layer with the upper portion of the vertically lapped material being above the absorbent layer and the lower portion of the vertically lapped material being below the absorbent layer. The at least one layer of the vertically lapped material can comprise a first and second vertically lapped material and the wound dressing further comprises an absorbent layer, wherein the first vertically lapped material is positioned below the absorbent layer, the first vertically lapped material having a perimeter larger than a perimeter of the absorbent layer, and wherein the second vertically lapped material above the absorbent layer, the second vertically lapped material having a perimeter larger than the perimeter of the absorbent layer. The wound dressing in combination with a negative pressure source. The negative pressure source can be positioned within the wound dressing. The negative pressure source and/or electronic components can be positioned within or adjacent to a transmission layer. The negative pressure source and/or electronic components can be positioned within or adjacent to an absorbent layer. The wound dressing can further comprise a suction adapter positioned over an opening in the backing layer to provide negative pressure to the wound dressing. The suction adapter can comprise an elongate bridge containing a vertically lapped material.

Any of the features, components, or details of any of the arrangements or embodiments disclosed in this application, including without limitation any of the dressing embodiments, pump embodiments, and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIGS. 5A-5D illustrates an embodiment of a wound treatment system employing a wound dressing capable of absorbing and storing wound exudate to be used without negative pressure;

DETAILED DESCRIPTION

Figure 1:
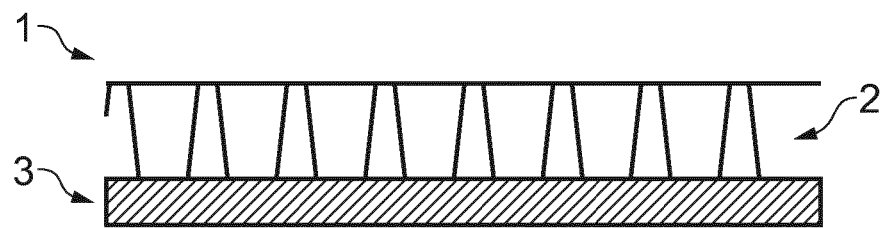
FIG. 1 illustrates an embodiment of a wound dressing containing 1) Top film, 2) Vertically lapped non-woven, 3) foam.

The disclosed technology relates to the wound dressing disclosed herein, and to methods and uses disclosed herein.

At least some embodiments of the disclosed technology disclosed herein are described below.

Embodiments disclosed herein relate to apparatuses and methods of treating a wound with or without reduced pressure, including optionally a source of negative pressure and wound dressing components and apparatuses. The apparatuses and components comprising the wound overlay and packing materials, if any, are sometimes collectively referred to herein as dressings. In some embodiments, the wound dressing can be provided to be utilized without reduced pressure.

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

As used herein a chronic wound is one that does not heal in an orderly set of stages and in a predictable amount of time the way most wounds do; wounds that do not heal within three months are often considered chronic. For example a chronic wound may include an ulcer such as a diabetic ulcer, a pressure ulcer (or pressure injury), or venous ulcer.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as $-X$ mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., $-40$ mmHg is less than $-60$ mmHg). Negative pressure that is "more" or "greater" than $-X$ mmHg corresponds to pressure that is further from atmospheric pressure (e.g., $-80$ mmHg is more than $-60$ mmHg). In some embodiments, local ambient atmospheric pressure is used as a reference point, and such local atmospheric pressure may not necessarily be, for example, 760 mmHg.

The negative pressure range for some embodiments of the present disclosure can be approximately $-80$ mmHg, or between about $-20$ mmHg and $-200$ mmHg. Note that these pressures are relative to normal ambient atmospheric pressure, which can be 760 mmHg. Thus, $-200$ mmHg would be about 560 mmHg in practical terms. In some embodiments, the pressure range can be between about $-40$ mmHg and $-150$ mmHg. Alternatively a pressure range of up to $-75$ mmHg, up to $-80$ mmHg or over $-80$ mmHg can be used. Also in other embodiments a pressure range of below $-75$ mmHg can be used. Alternatively, a pressure range of over approximately $-100$ mmHg, or even $-150$ mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," International Application No. PCT/IB2013/002060, filed on Jul. 31, 2013 published as WO2014/020440, entitled "WOUND DRESSING," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21, 2011, U.S. Pat. No. 9,061,095, titled "WOUND DRESSING AND METHOD OF USE," and U.S. patent application Ser. No. 14/715,527, filed May 18, 2015, titled "FLUIDIC CONNECTOR FOR NEGATIVE PRESSURE WOUND THERAPY," the disclosures of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Patent Application No. PCT/EP2016/059329, filed on Apr. 26, 2016, entitled "REDUCED PRESSURE APPARATUSES", published as WO 2016/174048, on Nov. 3, 2016, the entirety of which is hereby incorporated by reference. In some of these embodiments, the pump or associate electronic components may be integrated into the wound dressing to provide a single article to be applied to the wound.

Vertically Lapped Material

Embodiments of the wound dressings disclosed herein incorporate vertically lapped material. For example, a vertically lapped material may refer to a material having a pleated or folded structure, where the pleats or folds extend vertically relative to a horizontal plane defined by the plane of the wound dressing. The wound dressings disclosed herein may comprise one or more layers which may comprise vertically lapped material. For example, a wound dressing may comprise a first layer comprising one or more absorbing layers of material, each absorbing layer of material comprising a vertically lapped material. In other examples, the wound dressing may comprise a first layer comprising one or more non-absorbent layers of material, each non-absorbent layer of material comprising a vertically lapped material. Optionally, the wound dressings disclosed herein may comprise a second layer of material. The second layer of material may comprise a different material from the first layer of material. For example, the second layer of material may not comprise a vertically lapped material.

First Layer

The first layer of wound dressings disclosed herein may comprise two or more layers of the absorbing layer of material, the two or more layers of the absorbing layer of material comprising vertically lapped material stacked one on top of the other, wherein the two or more layers have the same or different densities or composition.

In some embodiments the wound dressings disclosed herein comprise only one layer of the absorbing layer of material, the one layer of the absorbing layer of material comprising vertically lapped material.

In some embodiments, the wound dressings disclosed herein comprise one or more layers of non-absorbent material, the one or more layers of non-absorbent material comprising vertically lapped material. In some embodiments, two or more layers of the non-absorbent material comprising vertically lapped material stacked one on top of the other, wherein the two or more layers have the same or different densities or composition.

In one embodiment the vertically lapped material has been slitted. The process of slitting is known to the skilled person. Slitting may include a process of creating a long, narrow cut or opening within the vertically lapped material.

Slitting through the thickness of the vertically lapped material may use traditional non-woven slitting methods such as; rotary knife, circular blade, bansaw, hotknife or a multi-blade slitter.

Novel cutting methodologies such as plasma, laser or ultrasonic may also be used.

The first layer may have a pleated structure having a depth determined by the depth of pleats or by the slitting width.

The first layer of material may be a moldable, lightweight, fiber-based material, blend of material or composition layer.

The first layer may be composed of manufactured fibres from synthetic, natural or inorgainic polymers, natural fibres of a cellulosic, proteinaceous or mineral source.

For example, the first layer of material may comprise one or more of cotton fibers, polyester, polyolefin, polyamide, polyaramide, acrylic, cellulosic, ramie, or any other fibrous material.

The absorbing layer of material may be a blend of natural or synthetic, organic or inorganic fibers, and binder fibers, or bicomponent fibres, typically PET with a low melt temperature PET coating to soften at specified temperatures and to act as a bonding agent in the overall blend. Such materials are known in the art.

In one embodiment the absorbing layer of material may be a blend of 5 to 95 wt % thermoplastic polymer, and 5 to 95 wt % of a cellulose or derivative thereof (typically ethyl celluose and/or propyl cellulose).

In one embodiment the absorbing layer of material may be a blend of 5 to 60 wt % thermoplastic polymer, and 40 to 95 wt % of a cellulose or derivative thereof thereof (typically ethyl celluose and/or propyl cellulose).

The cellulose material may include hydrophilically modified cellulose such as; carboxymethyl cellulose (CMC), ethyl celluose, propyl cellulose, hydroxyethyl cellulose, hydroxypropyl cellulose, carboxyethyl sulphonate cellulose or mixtures thereof.

Second Layer

In some embodiments the wound dressings disclosed herein comprise a second layer. The second layer may be foam or a dressing fixative.

The foam is known in the art and may include a polyurethane foam.

In one embodiment the wound dressing further comprises a layer of a superabsorbent fibre, or a viscose fibre or a polyester fibre. In some embodiments, the second layer can comprise a layer of a superabsorbent fibre, or a viscose fibre or a polyester fibre. In other embodiments, the layer of a superabsorbent fibre, or a viscose fibre or a polyester fibre can be used in addition to the second layer described herein.

Fibre types may consist of synthetic polymers, natural polymers, cellulosic, protienacous or mineral and may be regenerated or recycled.

Wound Dressing

The wound dressing may be suitable to include within a negative pressure wound apparatus.

The wound dressing may be suitable to include within a non-negative pressure wound apparatus.

The dressing is designed to be easy to apply and may be removed in one piece.

In one embodiment the dressing does not require secondary retention.

The wound dressing may be wrapped and sterile.

The wound dressing may be a negative pressure wound dressing, or a non-negative pressure wound dressing.

The disclosed technology in one embodiment relates to a non-negative pressure wound therapy kit comprising the wound dressing.

The wound dressing may be used as the dressing component of a negative pressure wound dressing apparatus. The apparatus in different embodiments comprises a canister and is free of the canister.

In one embodiment the disclosed technology relates to a negative pressure wound therapy kit comprising a wound dressing outlined above and a negative pressure source configured to be fluidically connected to the wound dressing.

In one embodiment the disclosed technology relates to a method of providing negative pressure wound therapy to a wound, the method comprising:
  placing the wound dressing outlined above over a wound;
  forming a fluid flow path between the wound dressing and a negative pressure source; and
  operating the negative pressure source to provide negative pressure to the wound.

In one embodiment the disclosed technology relates to a method of operating a negative pressure wound system, the method comprising:
  operating a negative pressure source fluidically connected to a wound dressing outlined above, the wound dressing configured to be positioned over a wound.

The wound dressing may be used as wound dressing for a non-negative pressure wound dressing apparatus.

In one embodiment the disclosed technology relates to a method of placing the wound dressing disclosed herein comprising an absorbent layer, wherein the wound dressing configured to be positioned over a wound, and exudate may be removed by evaporating exudate through an absorbent layer.

The wound dressing disclosed herein may be placed over a wound for 1 to 10 days, typically 3-7 days. The wound dressing may be replaced either when the wound is in the opinion of the HCP sufficiently healed, and/or when any absorbent layer/canister is saturated/full. The wound dressing can be replaced and/or canister can be replaced leaving the original dressing in place.

In one embodiment the wound dressing may be prepared by a method of manufacturing a wound dressing, the method comprising:
  (i) forming a vertically lapped material comprising an absorbing layer of material, and
  (ii) attaching the absorbing layer or material from step (i) with a second layer of material,
wherein the first layer from step (i) being constructed from at least one layer of non-woven textile fibers, the non-woven textile fibers being folded into a plurality of folds to form a pleated structure; and
  the second layer of material is temporarily or permanently connected to the first layer of material.

In one embodiment the wound dressing may be prepared by a method of manufacturing a wound dressing, the method comprising:
  (i) forming a vertically lapped material comprising an absorbing layer of material, and
  (ii) attaching the absorbing layer or material from step (i) with a second layer of material,
wherein the first layer from step (i) being constructed from at least one layer of non-woven textile fibers, the non-woven textile fibers being folded into a plurality of folds to form a pleated structure; and
the second layer of material is temporarily or permanently connected to the first layer of material, and
wherein the thickness of the wound dressing is between 1 and 20 mm, or 2 to 10 mm, or 3 to 7 mm.

In one embodiment the wound dressing may be prepared by a method of manufacturing a wound dressing, the method comprising:
  (i) forming a vertically lapped material comprising a non-absorbing layer of material, and
  (ii) attaching the non-absorbing layer or material from step (i) with a second layer of material,
wherein the first layer from step (i) being constructed from at least one layer of non-woven textile fibers, the non-woven textile fibers being folded into a plurality of folds to form a pleated structure; and
  the second layer of material is temporarily or permanently connected to the first layer of material.

In one embodiment the wound dressing may be prepared by a method of manufacturing a wound dressing, the method comprising:
  (i) forming a vertically lapped material comprising an absorbing layer of material,
  wherein the first layer from step (i) being constructed from at least one layer of non-woven textile fibers, the non-woven textile fibers being folded into a plurality of folds to form a pleated structure.

In one embodiment the wound dressing may be prepared by a method of manufacturing a wound dressing, the method comprising:
  (i) forming a vertically lapped material comprising a non-absorbing layer of material,
  wherein the first layer from step (i) being constructed from at least one layer of non-woven textile fibers, the non-woven textile fibers being folded into a plurality of folds to form a pleated structure.

In one embodiment the non-negative pressure wound therapy kit comprises or consists of:
  a wound dressing disclosed herein; and
  a dressing fixative (may also be defined as a secondary retention).

The dressing fixative may be securing means that can include adhesive (e.g. with pressure-sensitive adhesive) and non-adhesive, and elastic and non-elastic straps, bands, loops, strips, ties, bandages, e.g. compression bandages, sheets, covers, sleeves, jackets, sheathes, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheathes, wraps, stockings and hose that are a compressive fit over a limb wound to apply suitable pressure to it when the therapy is applied in this way.

Such securing means may each be laid out over the wound dressing to extend beyond the periphery of the backing layer of the wound dressing, and as appropriate will be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound, Such securing means may each be integral with the other components of the dressing, in particular the backing layer. Alternatively, it may be permanently attached or releasably attached to the dressing, in particular the backing layer, with an adhesive film, for example, or these components may be a Velcro™, push snap or twist-lock fit with each other.

The securing means and the dressing may be separate structures, permanently unattached to each other In one embodiment the dressing fixative may include a bandage, tubular or compression bandage, tape, gauze, or backing layer.

In one embodiment the disclosed technology relates to a non-negative pressure method of providing wound therapy to a wound, the method comprising: placing the wound dressing disclosed herein over a wound; and securing the wound dressing with a dressing fixative such as a bandage, tape, gauze, or backing layer.

Non-Woven

In one embodiment the wound dressing comprises the absorbing layer of material connected directly to a second layer by lamination or by an adhesive, and the second layer is connected to a dressing fixative layer.

The wound dressing may optionally further comprise other layers such as a backing layer, or an adhesive layer, or a supplementary absorbent layer. In one embodiment the wound dressing comprises at least one or at least two of the optional other layers.

Backing Layer

In one embodiment the wound dressing further comprises a backing layer.

The backing layer may be transparent or opaque film. The transparent backing layer (may be referred to as top layer) may provide the healthcare professional (HCP) with the ability to carry out regular assessments of the wound site including the peri-wound area and the wound itself without the need to lift or remove the dressing. This may allow the HCP to react early to signs that could potentially delay the healing process. Encouraging healing and reducing the chance of infection can lead to shorter recovery times and lower treatment costs.

The material used to form the transparent backing layer may have a high Moisture Vapor Transmission Rate (MVTR), thereby allowing unwanted moisture to transpire and helps prevent infection and maceration.

The transparent backing layer may be waterproof, thereby enabling the patient to shower/bathe with the dressing in situ.

The transparent backing layer may provide a barrier against bacteria, including methicillin-resistant *Staphylococcus aureus* (MRSA). This will reduce the incidences of surgical site infections (SSI) and healthcare associated infections (HAI), reducing possible associated costs to healthcare provider and extended hospital stay for the patient.

The transparent backing layer may further act as a barrier to water and dirt.

The backing layer may be a film. In one embodiment the backing layer is a polyurethane film. The polyurethane film may be optionally functionalised with additives such as antimicrobial agents, odour control, pigments, dyes or UV disruptors. The backing layer may be a monolithic or microporous film or a foam. It may also be an impermeable film.

In one embodiment the wound dressing does not further comprise a backing layer.

Adhesive Layer

In one embodiment the wound dressing further comprises an adhesive layer.

The adhesive layer may be located:
(i) between the first layer and the second layer of the disclosed technology and/or
(ii) at the peripheral edges of the backing layer if present (typically a transparent film layer) that extend beyond the peripheral edges of any absorbent layer present.

The adhesive may be a silicone adhesive or an acrylic adhesive.

The adhesive may be spread evenly across the surfaces of the first and second layer of the disclosed technology. An even spread of adhesive may ensure that the surfaces of the layers of the disclosed technology are securely joined.

If the adhesive layer is on the underside of the backing layer it provides adhesion to the wound dressing to a peri-wound area.

Alternatively, the adhesive can be spread in a pattern to increase breathability of the film and improve comfort upon removal.

The adhesive used may be low allergy. This type of adhesive reduces the trauma upon removal of the dressings and/or lessens the risk of an allergic reaction.

In one embodiment the wound dressing may include a number of layers that are built up in a generally laminar fashion to form a dressing having a relatively planar form. Examples of such a wound dressing may for instance be disclosed in WO2013/007793.

In one embodiment the wound dressing may include a border region extending around the outer periphery of the dressing and a raised central region (or pouch) in the centre of the dressing (in plan view). The precise dimensions of the border region and the central region may be predetermined to suit a particular wound or particular wound type.

Alternatively in another embodiment there may be no border region required. Here the border region has the general function of providing an area for sealingly engaging with a patient's skin surrounding a wound site to form a sealed cavity over the wound site. The central region is the location of further functional elements of the wound dressing.

The wound dressing disclosed herein may include a perforated wound contact layer and a top film. Further components of the wound dressing optionally include in no particular order:

A layer of polyurethane hydrocellular foam of a suitable size to cover the wound and peri-wound, A layer of activated charcoal cloth of similar or slightly smaller dimensions than, to allow for odour control with limited aesthetic impact on the wound side, A layer of superabsorbent air-laid material containing cellulose fibres and a superabsorbent polyacrylate particulates, of dimensions slightly larger than to allow for an overlap of superabsorbent material acting as leak prevention, A layer of three-dimensional knitted spacer fabric, providing protection from pressure, while allowing partial masking of the top surface of the superabsorber, where coloured exudate would remain. In this embodiment this is of smaller dimension (in plan view) than the layer, to allow for visibility of the edge of the absorbent layer, which can be used by clinicians to assess whether the dressing needs to be changed. In this embodiment the wound contact layer may be a perforated polyurethane film that is coated with a skin-compatible adhesive, such as pressure sensitive acrylic adhesive or silicone adhesive.

In separate embodiments the wound dressing comprises two, three, or all of the layers disclosed above.

In one embodiment the wound dressing comprises all of the layers disclosed above in the order of a layer of polyurethane hydrocellular foam to the three-dimensional knitted spacer fabric in the specified order.

Alternatively the wound contact layer may be formed from any suitable polymer, e.g. silicone, ethylvinyl acetate, polyethylene, polypropylene, or polyester, or a combination thereof. The skin-compatible adhesive is coated on the lower side of the layer, i.e. the side that is to contact the patient. Aptly the adhesive is coated as a continuous layer on the underside of the layer. The adhesive may be coated in a semi-continuous layer such as in a pattern such as a chequerboard pattern, polka dot pattern, herring bone pattern, mesh pattern or other suitable pattern.

In one embodiment the wound dressing may comprise as disclosed herein 1) Top film, 2) Vertically lapped non-woven, 3) foam.

In one embodiment the wound dressing may comprise as disclosed herein 1) Top film, 2) Vertically lapped non-woven 3) treated vertically lapped non-woven.

In one embodiment the wound dressing may comprise as disclosed herein 1) Top film, 2) traditional non-woven or foam, 3) Vertically lapped non-woven, 4) traditional non-woven or foam.

The following examples provide illustrations of the disclosed technology. These examples are non-exhaustive and are not intended to limit the scope of the disclosed technology.

EXAMPLES

Example 1: is a dressing prepared containing 1) Top film, 2) Vertically lapped non-woven, 3) foam, these components may be held together using a hot melt adhesive which is affixed using a lamination process by a process known to the skilled person. The wound dressing is represented by FIG. 1.

Figure 2:
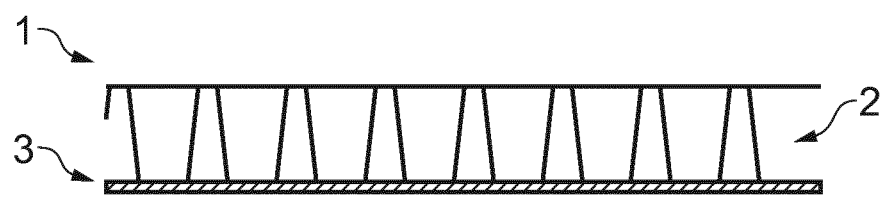
FIG. 2 illustrates an embodiment of is a wound dressing containing 1) Top film, 2) Vertically lapped non-woven 3) treated vertically lapped non-woven.

Example 2: is a dressing may consist of 1) Top film, 2) Vertically lapped non-woven 3) treated vertically lapped non-woven. In this example the vertically lapped non-woven is heat treated using a calendar or hot knife to produce a smooth surface. The wound dressing is represented by FIG. 2.

Figure 3:
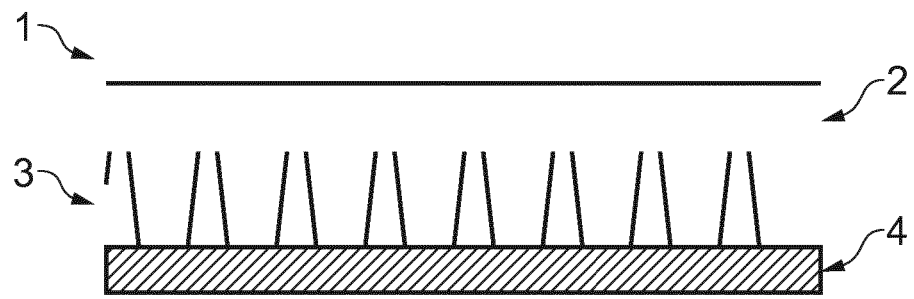
FIG. 3 illustrates an embodiment of a wound dressing containing 1) Top film, 2) traditional non-woven or foam, 3) Vertically lapped non-woven, 4) traditional non-woven or foam.

Example 3: construction may be 1) Top film, 2) traditional non-woven or foam, 3) Vertically lapped non-woven, 4) traditional non-woven or foam, whereby the top film and the vertically lapped non-woven are affixed using pressure sensitive adhesive and the vertically lapped non-woven and the traditional non-woven affixed through a needling technique. The wound dressing is represented by FIG. 3.

Example 4: is the same as Example 1, except the layers may be affixed together using a heat and pressure lamination process.

Example 5: is the same as Example 1 except the layers may be affixed together using a hot melt adhesive and a pressure sensitive adhesive.

Example 6: is the same as Example 2 where the vertically lapped non-woven may be surface treated, for example with a coating which may contain actives ingredients such as anti-microbial.

Figure 4A:
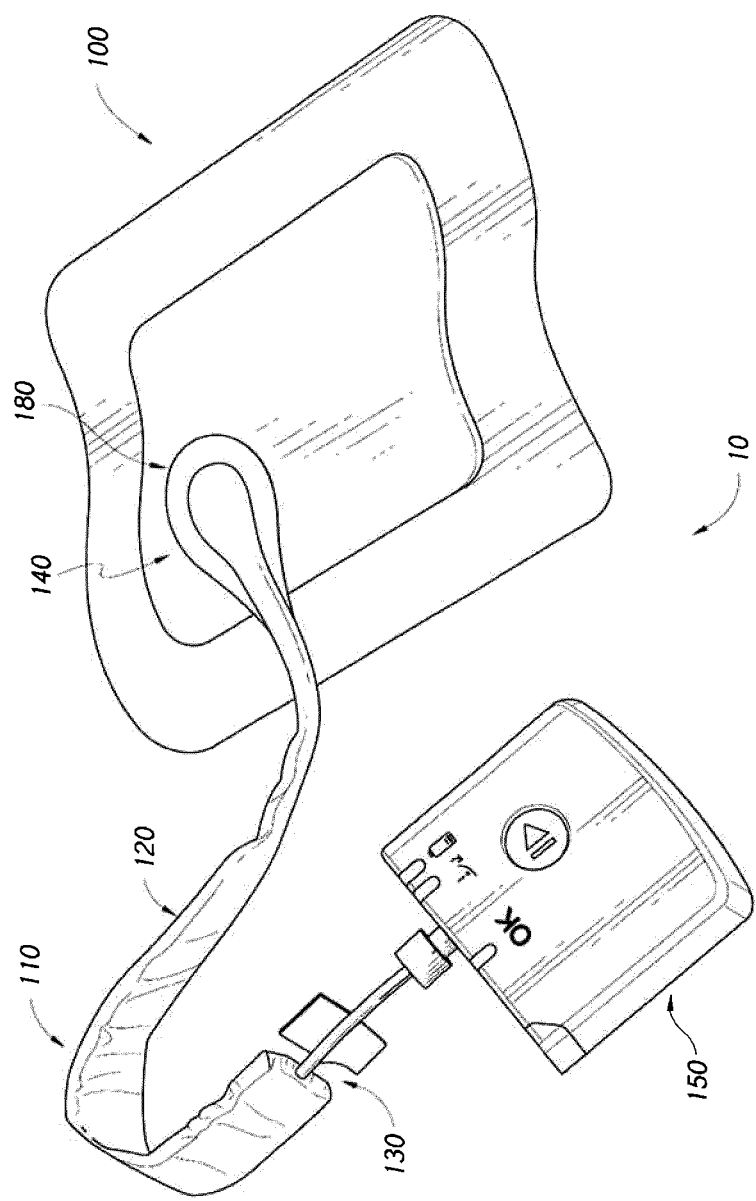
FIG. 4A illustrates an embodiment of a negative pressure wound treatment system employing a flexible fluidic connector and a wound dressing capable of absorbing and storing wound exudate.
Figure 4B:
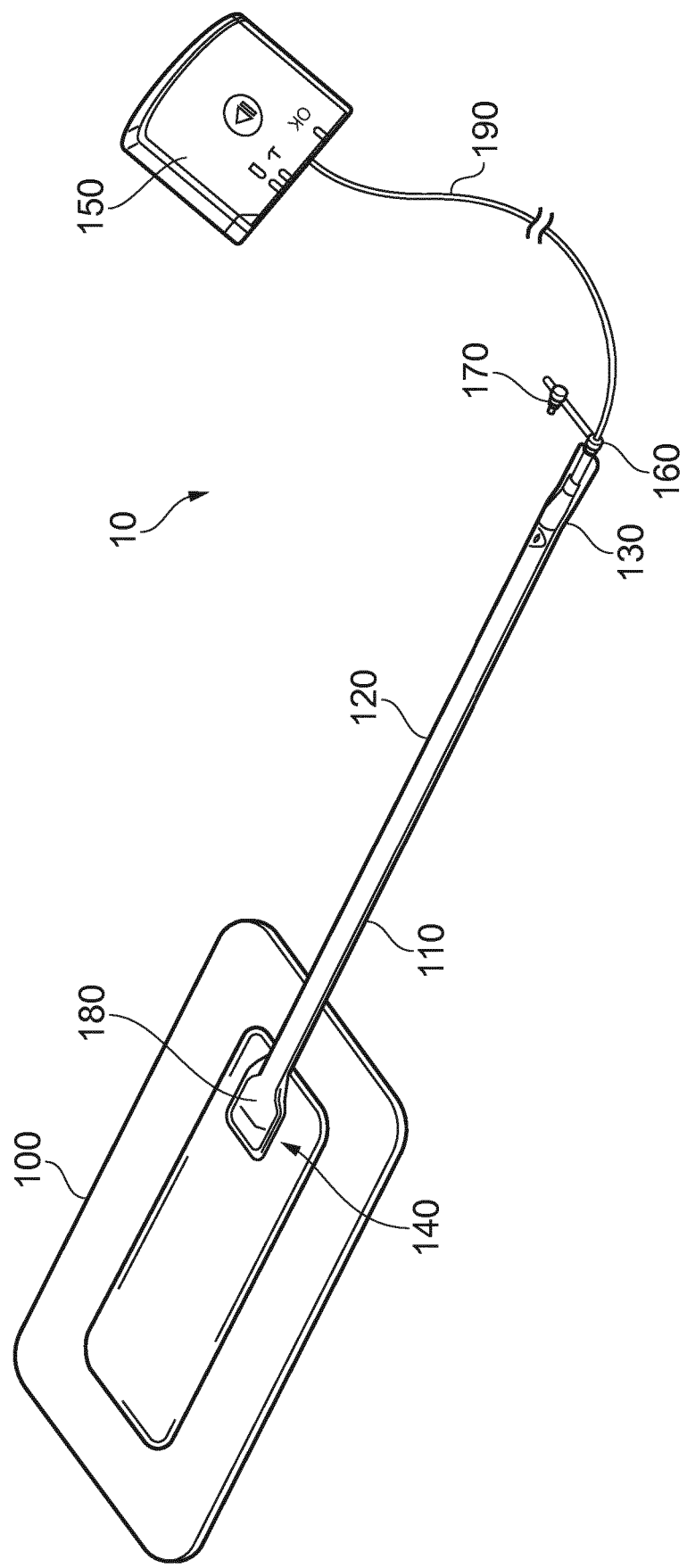
FIG. 4B illustrates an embodiment of a negative pressure wound treatment system employing a flexible fluidic connector and a wound dressing capable of absorbing and storing wound exudate.

FIGS. 4A-B illustrate embodiments of a negative pressure wound treatment system 10 employing a wound dressing 100 in conjunction with a fluidic connector 110. Additional examples related to negative pressure wound treatment comprising a wound dressing in combination with a pump as described herein may also be used in combination or in addition to those described in U.S. Pat. No. 9,061,095, which is incorporated by reference in its entirety. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 4A-4B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 4C:
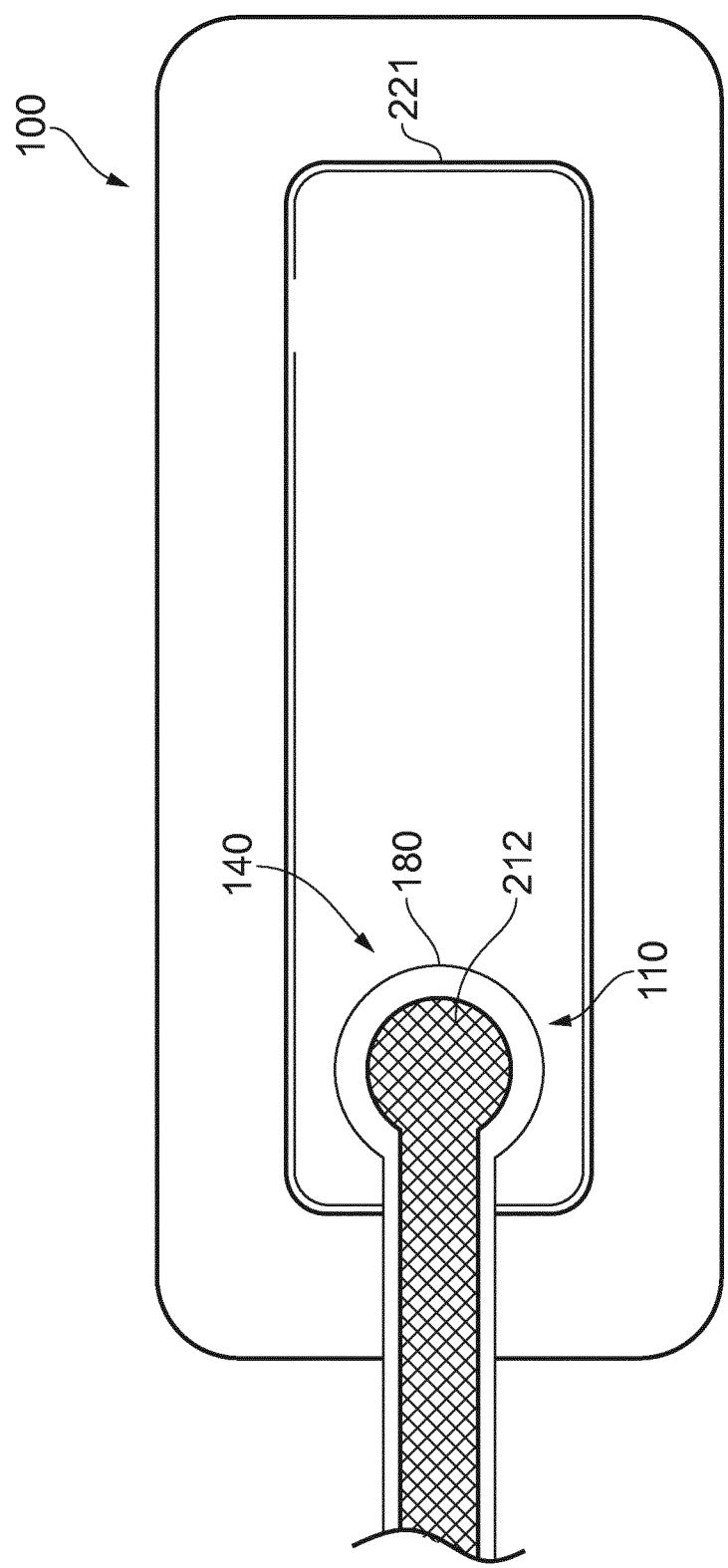
FIG. 4C illustrates an embodiment of a negative pressure wound treatment system employing a flexible fluidic connector and a wound dressing capable of absorbing and storing wound exudate.

As shown in FIG. 4C, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

Figure 4D:
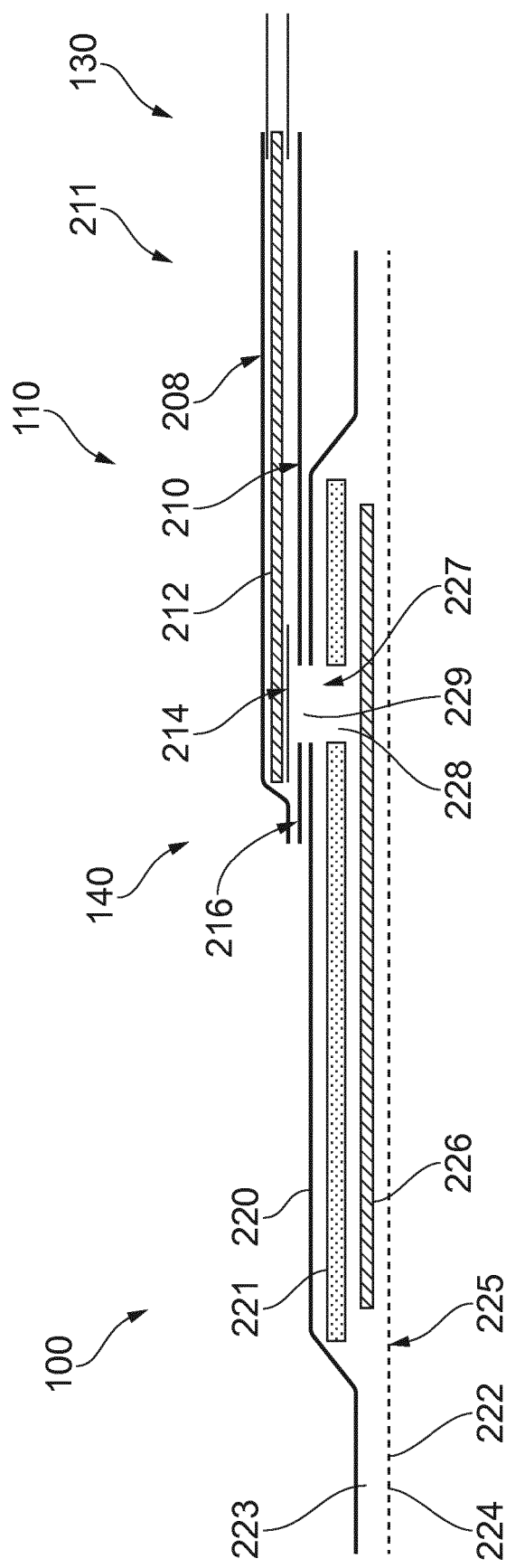
FIG. 4D illustrates a cross section of an embodiment of a fluidic connector connected to a wound dressing.
Figure 5E:
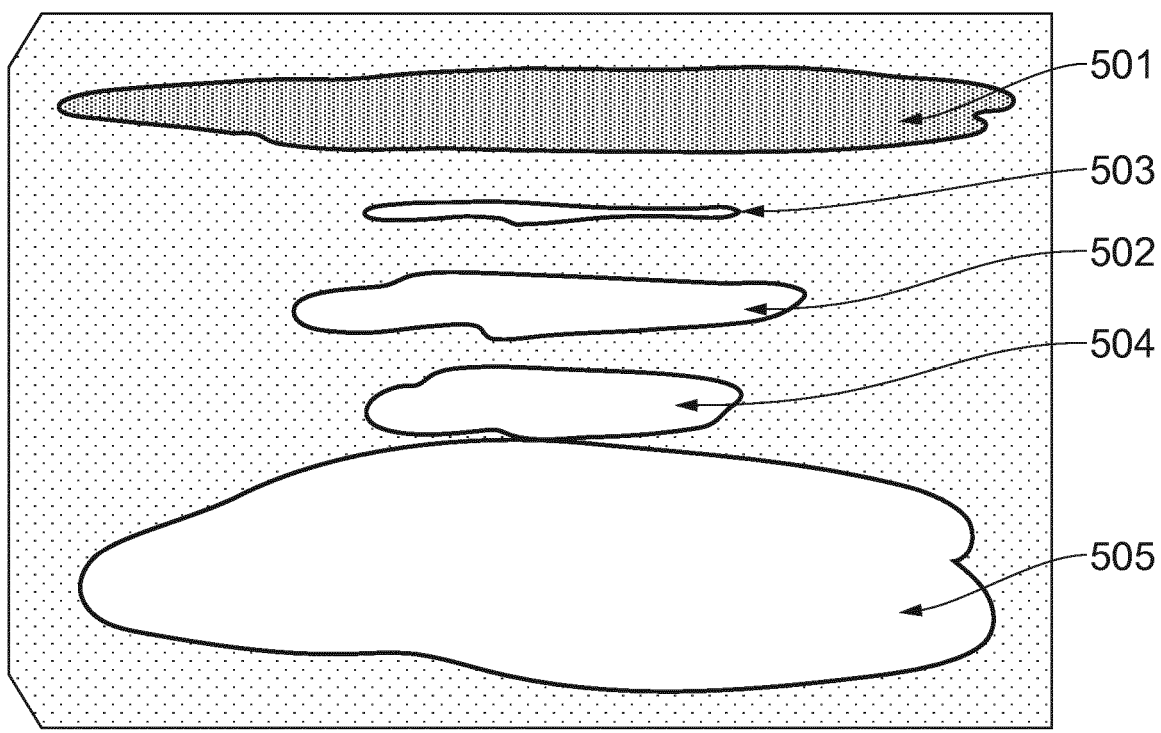
FIG. 5E illustrates a cross section of an embodiment of a wound treatment system employing a wound dressing capable of absorbing and storing wound exudate to be used without negative pressure.

FIG. 4D illustrates a cross-section through a wound dressing 100 similar to the wound dressing 10 as shown in FIG. 4B and described in International Patent Publication WO2013175306 A2, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 4D, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A transmission layer 226 can be located above the wound contact layer 222. In some embodiments, the transmission layer can be a porous material. As used herein the transmission layer can be referred to as a spacer layer and the terms can be used interchangeably to refer to the same component described herein. This transmission layer 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used. The three dimensional material can comprise a 3D spacer fabric material similar to the material described in International Application WO 2013/175306 A2 and International Application WO2014/020440, the disclosures of which are incorporated by reference in their entireties.

In some embodiments, the layer 226 can comprise a vertically lapped material as described previously herein and illustrated in FIGS. 1-3. In some embodiments, the vertically lapped material can include a first layer of an absorbing layer of material. In some embodiments, the layer 226 can comprise a first layer of a vertically lapped non-absorbing layer of material. In some embodiments, the first layer can optionally be temporarily or permanently attached to a second layer of material as described herein. The first layer can be constructed from at least one layer of non-woven textile fibers. The non-woven textile fibers can be folded into a plurality of folds to form a pleated structure. In some embodiments, a depth of the pleats of the pleated structure that has been slit can determine a thickness of the first layer of material. In some embodiments, the thickness of the wound dressing with vertically lapped material can be between 1 and 20 mm (or 2 to 10, or 3 to 7 mm). In some embodiments, the thickness of the vertically lapped material can be between 1 and 10 mm (or 2 to 7 mm). In some embodiments, the second layer of the vertically lapped material can be temporarily or permanently connected to the first layer of material. In some embodiments, the second layer can include a single or multi-layer construction. In some embodiments, the vertically lapped material can be formed from hydrophobic and/or hydrophilic fibers. The selection of fibers can vary the fluid handling properties of the vertically lapped material.

In some embodiments, a layer 221 of absorbent material is provided above the transmission layer 226. The absorbent material, which can comprise a foam or non-woven natural or synthetic material, and which may optionally comprise a super-absorbent material, forms a reservoir for fluid, particularly liquid, removed from the wound site. In some embodiments, the layer 221 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 or Chem-Posite™11C-450. In some embodiments, the absorbent layer 221 may comprise a composite comprising superabsorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

In some embodiments, the absorbent layer 221 can comprise a vertically lapped material with a first layer of an absorbing layer of material. The absorbing vertically lapped material can contain a super absorbent material or super absorbent fibers. In some embodiments, one or more layers of vertically lapped material may be used for both layers 226 and 221. In such embodiments, the vertically lapped material can allow transmission of fluid including liquid and gas away from a wound site into upper layers of the wound dressing and can provide a reservoir for fluid, particularly liquid, removed from the wound site.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Optionally, the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 4D a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 4D. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described with reference to FIGS. 8A-8B and in International Patent Publication WO2014/020440, the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way, an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments, the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIGS. 4C-4D, the absorbent layer 221 may define a smaller perimeter than that of the backing layer 220, such that a boundary or border region is defined between the edge of the absorbent layer 221 and the edge of the backing layer 220.

As shown in FIG. 4D, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for embodiments with a single fluidic connector 110 and through hole, it may be preferable for the fluidic connector 110 and through hole to be located in an off-center position as illustrated in FIG. 4C. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 4A-4B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments, the upper surface and the lower surface may be formed from the same piece of material. In some embodiments, the sealing surface 216 may comprise at least one aperture 229 therein to communicate with the wound dressing. In some embodiments, the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer. In other embodiments, the sealing surface 216 may be positioned over an orifice in the cover layer and an aperture in the absorbent layer 221, permitting the fluidic connector 110 to provide air flow through the transmission layer 226. In some embodiments, the bridge 211 may comprise a first fluid passage 212 in communication with a source of negative pressure, the first fluid passage 212 comprising a porous material which may be the same or different than the porous layer 226 described previously. In some embodiments, the porous material or transmission material can be a vertically lapped material as described herein. In some embodiments, the porous material or transmission material can be a 3D knitted material. The bridge 211 is preferably encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 100 similar to the suction adapter as described in U.S. application Ser. No. 13/381,885, filed Dec. 20, 2011, entitled "APPARATUSES AND METHODS FOR NEGATIVE PRESSURE WOUND THERAPY," and patented as U.S. Pat. No. 8,801,685, which is incorporated by reference herein in its entirety.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, vertically lapped material, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a vertically lapped material. These materials selected are preferably suited to channeling wound exudate away from the wound and for transmitting negative pressure or vented air to the wound site, and may also confer a degree of kinking or occlusion resistance to the fluid passage 212. In some embodiments, the wicking fabric may have a vertically lapped material, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm thick; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid barrier and to ensure that no liquids are able to escape from the wound dressing 100. The filter element 214 may also function as a bacterial barrier. Typically the pore size is 0.2 µm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments, filter element 214 comprises a support layer and an acrylic co-polymer membrane formed on the support layer. Preferably the wound dressing 100 according to certain embodiments uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

Similar to the embodiments of wound dressings described above, some wound dressings comprise a perforated wound contact layer with silicone adhesive on the skin-contact face and acrylic adhesive on the reverse. Above this bordered layer sits a transmission layer. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

FIGS. 5A-5D illustrates various embodiments of a wound dressing that can be used for healing a wound without negative pressure. FIG. 5E illustrates a cross-section of the wound dressing in FIGS. 5A-5D. As shown in the dressings of FIGS. 5A-E, the wound dressings can have multiple layers similar to the dressings described with reference to FIGS. 4A-D except the dressings of FIGS. 5A-E do not include a port or fluidic connector. The wound dressings of FIGS. 5A-E can include a cover layer 501 and wound contact layer 505 as described herein. The wound dressing can include various layers positioned between the wound contact layer 505 and cover layer 501. For example, the dressing can include one or more absorbent layers 502 or one or more transmission layers 504 as described herein with reference to FIGS. 4A-D.

In some embodiments, the one or more transmission layers 504 or the one or more absorbent layers 502 can comprise a vertically lapped material as described previously herein and illustrated in FIGS. 1-3. In some embodiments, the vertically lapped material can include a first layer of an absorbing layer of material. In other embodiments, the vertically lapped material can include a first layer of a non-absorbing layer of material. In some embodiments, the first layer can optionally be temporarily or permanently attached to a second layer of material as described herein. The first layer can be constructed from at least one layer of non-woven textile fibers. The non-woven textile fibers can be folded into a plurality of folds to form a pleated structure. In some embodiments, a depth of the pleats of the pleated structure that has been slit can determine a thickness of the first layer of material. In some embodiments, the thickness of the wound dressing with vertically lapped material can be between 1 and 20 mm (or 2 to 10, or 3 to 7 mm). In some embodiments, the thickness of the vertically lapped material can be between 1 and 10 mm (or 2 to 7 mm). In some embodiments, the second layer of the vertically lapped material can be temporarily or permanently connected to the first layer of material. In some embodiments, the second layer can include a single or multi-layer construction. In some embodiments, the vertically lapped material can be formed from hydrophobic and/or hydrophilic fibers. The selection of fibers can vary the fluid handling properties of the vertically lapped material.

In some embodiments, the absorbent layer 502 can comprise a vertically lapped material with a first layer of an absorbing layer of material. The absorbing vertically lapped material can contain a super absorbent material or super absorbent fibers. In some embodiments, one or more layers of vertically lapped material may be used for both layers 502 and 504. In such embodiments, the vertically lapped material can allow transmission of fluid including liquid and gas away from a wound site into upper layers of the wound dressing and can provide a reservoir for fluid, particularly liquid, removed from the wound site.

In some embodiments, additional layers such as another transmission layer or an obscuring layer 503 may be provided over the absorbent layer 503 and beneath the backing layer 501. Additionally, some embodiments related to wound treatment comprising a wound dressing described herein may also be used in combination or in addition to those described in U.S. Application Publication No. 2014/0249495, filed May 21, 2014, entitled "WOUND DRESSING AND METHOD OF TREATMENT" the disclosure of which are hereby incorporated by reference in its entirety, including further details relating to embodiments of wound dressings, the wound dressing components and principles, and the materials used for the wound dressings.

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. Additionally, some embodiments related to wound treatment comprising a wound dressing described herein may also be used in combination or in addition to those described in International Application WO 2016/174048 and International Patent Application PCT/EP2017/055225, filed on Mar. 6, 2017, entitled "WOUND TREATMENT APPARATUSES AND METHODS WITH NEGATIVE PRESSURE SOURCE INTEGRATED INTO THE WOUND DRESSING," the disclosure of which is hereby incorporated by reference in its entirety herein, including further details relating to embodiments of wound dressings, the wound dressing components and principles, and the materials used for the wound dressings and wound dressing components.

Figure 6A:
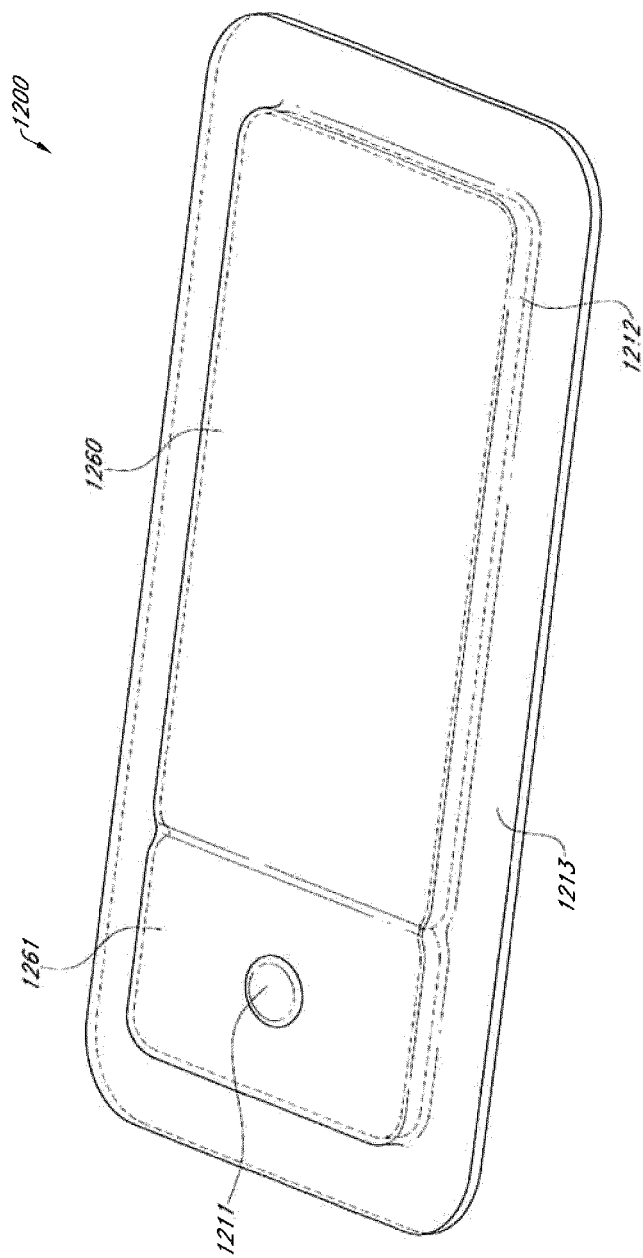
FIGS. 6A-6B illustrate an embodiment of a wound dressing incorporating the source of negative pressure and/or other electronic components within the wound dressing.
Figure 6B:
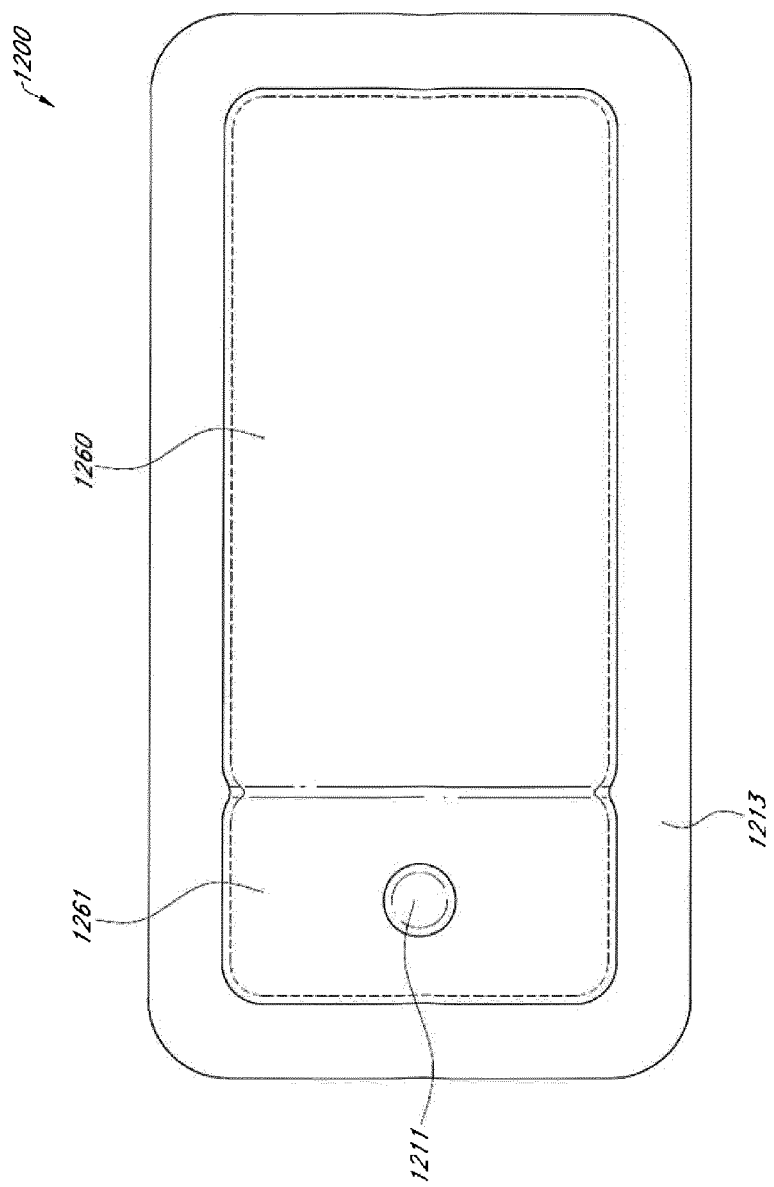

In some embodiments, the pump and/or other electronic components can be configured to be positioned adjacent to or next to the absorbent and/or transmission layers in the wound dressing so that the pump and/or other electronic components are still part of a single apparatus to be applied to a patient with the pump and/or other electronics positioned away from the wound site. FIGS. 6A-6B illustrates a wound dressing incorporating the source of negative pressure and/or other electronic components within the wound dressing. FIGS. 6A-6B illustrates a wound dressing 1200 with the pump and/or other electronics positioned away from the wound site. The wound dressing can include an electronics area 1261 and an absorbent area 1260. The dressing can comprise a wound contact layer (not shown) and a moisture vapor permeable film or cover layer 1213 positioned above the contact layer and other layers of the dressing. The wound dressing layers and components of the electronics area as well as the absorbent area can be covered by one continuous cover layer 1213 as shown in FIGS. 6A-6B.

The electronics area 1261 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 1261 can include a button or switch 1211 as shown in FIG. 6A-6B. The button or switch 1211 can be used for operating the pump (e.g., turning the pump on/off).

The absorbent area 1260 can include an absorbent material 1212 and can be positioned over the wound site. The electronics area 1261 can be positioned away from the wound site, such as by being located off to the side from the absorbent area 1260. The electronics area 1261 can be positioned adjacent to and in fluid communication with the absorbent area 1260 as shown in FIGS. 6A-6B. In some embodiments, each of the electronics area 1261 and absorbent area 1260 may be rectangular in shape and positioned adjacent to one another.

In some embodiments, additional layers of dressing material can be included in the electronics area 1261, the absorbent area 1260, or both areas. In some embodiments, the dressing can comprise one or more spacer or transmission layers and/or one or more absorbent layer positioned above the contact layer and below the wound cover layer 1213 of the dressing.

The dressing can comprise a wound contact layer (not shown), a transmission layer (not shown), an absorbent layer 1212 over the transmission layer, a moisture vapor permeable film or cover layer 1213 positioned above the wound contact layer, transmission layer, absorbent layer, or other layers of the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound. The one or more transmission layers assist in distributing negative pressure over the wound site and facilitating transport of wound exudate and fluids into the wound dressing. In some embodiments, the transmission layer can be formed at least partially from a three dimensional (3D) fabric. Further, an absorbent layer (such as layer 1212) for absorbing and retaining exudate aspirated from the wound can be utilized. In some embodiments, a superabsorbent material can be used in the absorbent layer 1212. In some embodiments, the absorbent includes a shaped form of a superabsorber layer. In some embodiments, the transmission layer and/or the absorbent layer can be formed at least partially from a vertically lapped material as described herein. The wound dressing layers of the electronics area and the absorbent layer can be covered by one continuous cover layer 1213. In some embodiments, the cover layer can include a moisture vapor permeable material that prevents liquid exudate removed from the wound and other liquids from passing through, while allowing gases through.

Figure 6C:
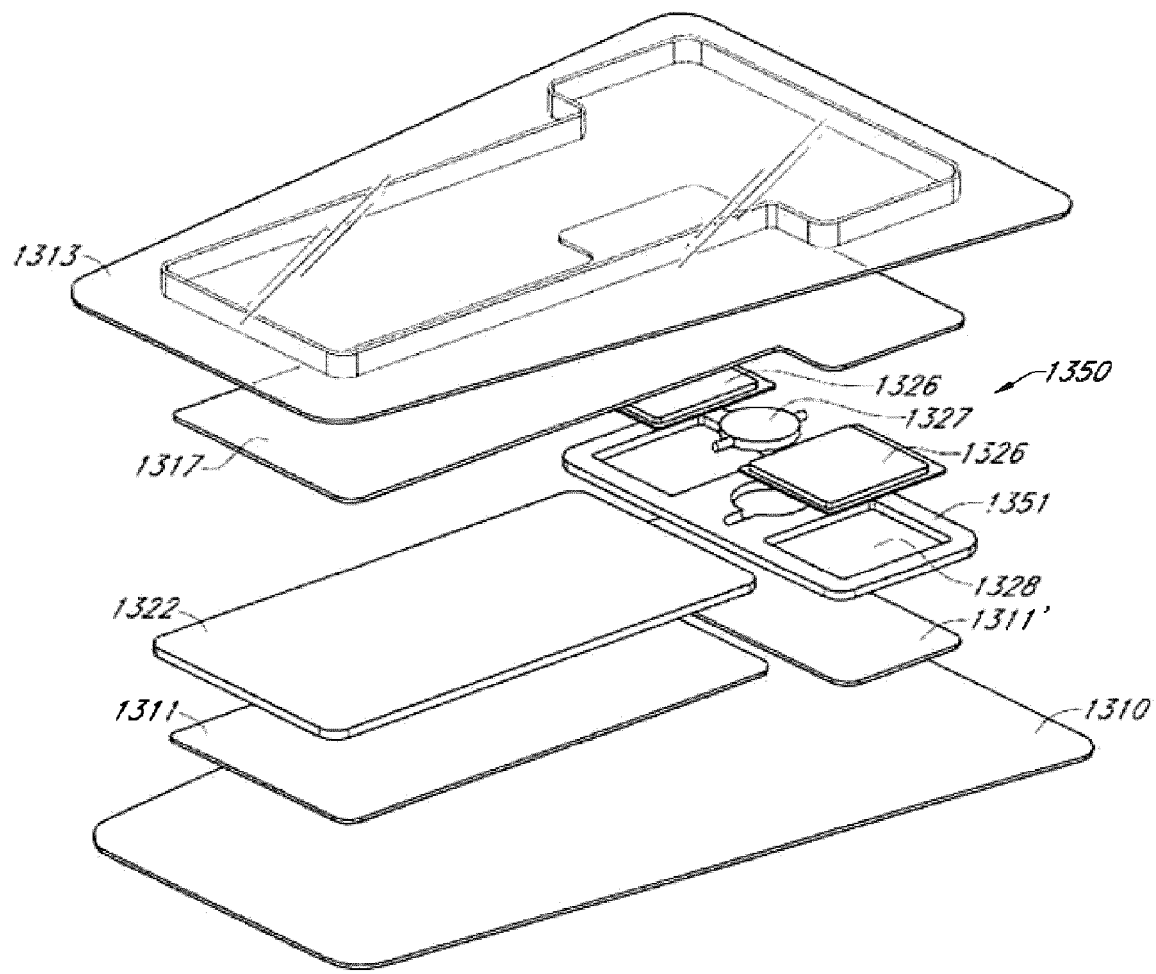
FIG. 6C illustrates an embodiment of layers of a wound dressing with the pump and electronic components offset from the absorbent area of the dressing.

FIG. 6C illustrates an embodiment of layers of a wound dressing with the pump and electronic components offset from the absorbent area of the dressing. As illustrated in FIG. 6C, the dressing can include a wound contact layer 1310 for placing in contact with the wound. Lower spacer or transmission layers 1311 and 1311' are provided above the wound contact layer 1310. In some embodiments, the transmission layer 1311 can be a separate layer from spacer layer 1311' as shown in FIG. 6C. The lower transmission layers 1311 and/or 1311' can assist in distributing pressure evenly to the wound surface and/or wicking fluid away from the wound. An absorbent layer 1322 can be positioned above the lower transmission layer 1311. A dressing layer 1351 can include cutouts or recesses 1328 for embedding the electronic components 1350 within the layer 1351. In some embodiments, the cutouts or recesses 1328 can be sized and shaped to embed a pump 1327, power source 1326, and/or other electronic components. In some embodiments, the layer 1351 can include multiple spacer or transmission layers stacked together. In some embodiments, the layer 1351 can include multiple spacer or transmission layers pieced together to surround the electronic components 1350. An upper transmission layer 1317 can be provided above the absorbent layer 1322, layer 1351, and/or electronic components 1350. In some embodiments, the one or more transmission layers can comprise a vertically lapped material as described previously herein and illustrated in FIGS. 1-3. In some embodiments, the vertically lapped material can include a first layer of an absorbing layer of material. In other embodiments, the vertically lapped material can include a first layer of a non-absorbing layer of material. In some embodiments, the first layer can optionally be temporarily or permanently attached to a second layer of material as described herein. The first layer can be constructed from at least one layer of non-woven textile fibers. The non-woven textile fibers can be folded into a plurality of folds to form a pleated structure. In some embodiments, a depth of the pleats of the pleated structure that has been slit can determine a thickness of the first layer of material. In some embodiments, the thickness of the wound dressing with vertically lapped material can be between 1 and 20 mm (or 2 to 10, or 3 to 7 mm). In some embodiments, the thickness of the vertically lapped material can be between 1 and 10 mm (or 2 to 7 mm). In some embodiments, the second layer of the vertically lapped material can be temporarily or permanently connected to the first layer of material. In some embodiments, the second layer can include a single or multi-layer construction. In some embodiments, the vertically lapped material can be formed from hydrophobic and/or hydrophilic fibers. The selection of fibers can vary the fluid handling properties of the vertically lapped material.

In some embodiments, the absorbent layer 1212 can comprise a vertically lapped material with a first layer of an absorbing layer of material. The absorbing vertically lapped material can contain a super absorbent material or super absorbent fibers. In some embodiments, one or more layers of vertically lapped material may be used for both the absorbent layer 1212 and one or more of the transmission layers 1311, 1311', 1351, and/or 1317. In such embodiments, the vertically lapped material can allow transmission of fluid including liquid and gas away from a wound site into upper layers of the wound dressing and can provide a reservoir for fluid, particularly liquid, removed from the wound site.

A cover layer or backing layer 1313 can be positioned over the upper transmission layer. The backing layer 1313 can form a seal to the wound contact layer 1310 at a perimeter region enclosing the transmission layers 1311, 1311', and 1317, the absorbent layer 1322, layer 1351, and electronic components 1350. In some embodiments, the backing layer 1313 can be a flexible sheet of material that forms and molds around the dressing components when they are applied to the wound. In other embodiments, the backing layer 1313 can be a material that is preformed or premolded to fit around the dressing components as shown in FIG. 6C.

Figure 7A:
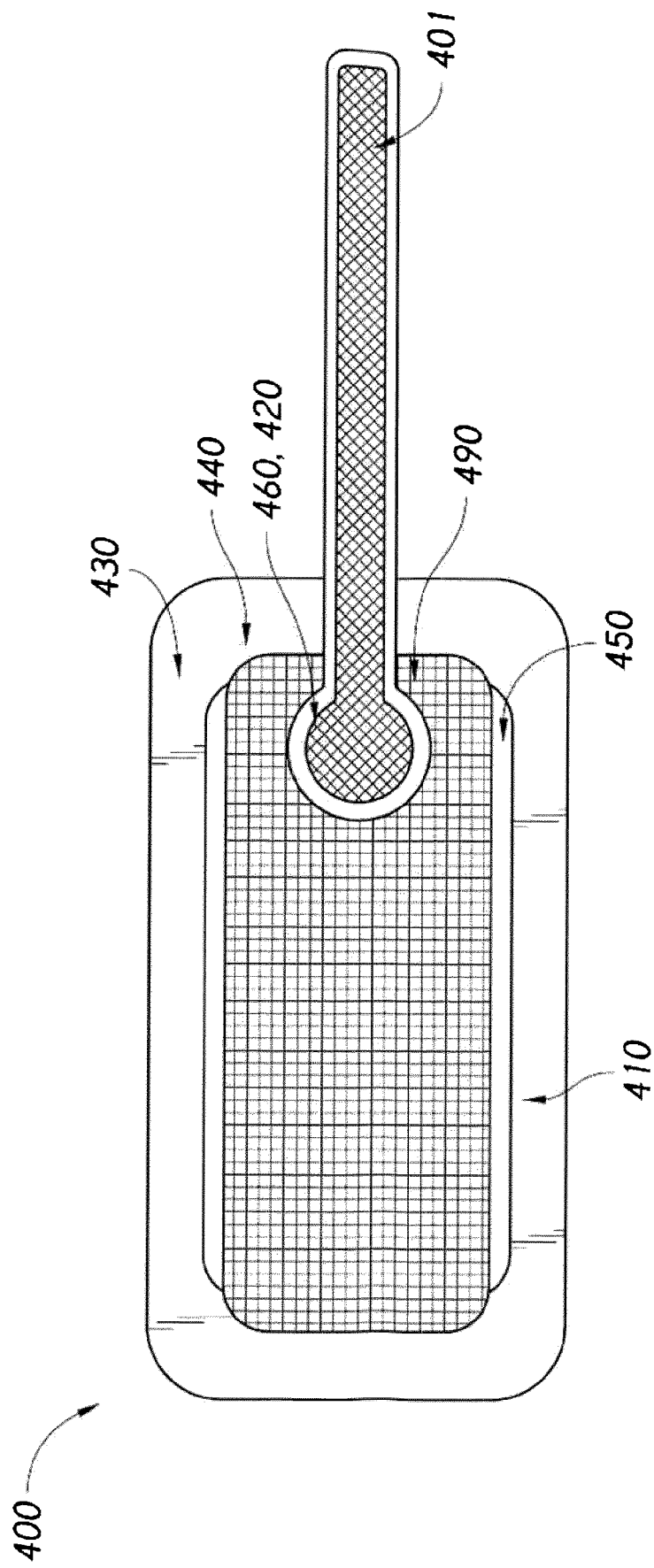
FIG. 7A illustrates an embodiment of a negative pressure wound treatment system employing a flexible fluidic connector and a wound dressing with a wrapped around spacer layer, the wound dressing capable of absorbing and storing wound exudate.

FIG. 7A illustrates an embodiment of a TNP wound treatment device comprising a wound dressing. As stated above, the wound dressing 400 can be any wound dressing embodiment disclosed herein or have any combination of features of any number of wound dressing embodiments disclosed herein. For example, the wound dressing 400 may be similar to a PICO single unit dressing available from Smith & Nephew as described previously. The wound dressing 400 and associated system may also be similar to the system described in FIGS. 4A-4D previously. Embodiments of the wound dressings, wound dressing components, wound treatment apparatuses and methods described herein and with reference to FIGS. 7A-7C may also be used in combination or in addition to those described in International Application No. PCT/EP2016/082353, filed Dec. 22, 2016, titled "NEGATIVE PRESSURE WOUND THERAPY APPARATUS," the disclosure of which is hereby incorporated by reference in its entirety.

The dressing 400 may be placed over a wound, and a port 460 (which together with conduit 401 may form a fluidic connector as described with respect to FIGS. 4A-4D) may be used to provide negative pressure from a vacuum source to the wound. In the embodiment shown in FIG. 4A the dressing 400 may be provided with at least a portion of the conduit 401 pre-attached to the port 460. For example, the port/conduit combination may be a flexible suction adapter as described herein with reference to FIGS. 4A-4D. In some embodiments, the pre-attached conduit 401 can connect to a conduit extension, for example, a tubing (not shown). Preferably, the dressing 400 is provided as a single article with all wound dressing elements (including the port 460 and conduit 401) pre-attached and integrated into a single unit. The wound dressing 400 may then be connected, via the conduit 401 and/or conduit extension, to a source of negative pressure such as the pump as described with reference to FIGS. 4A-4D.

Figure 7B:
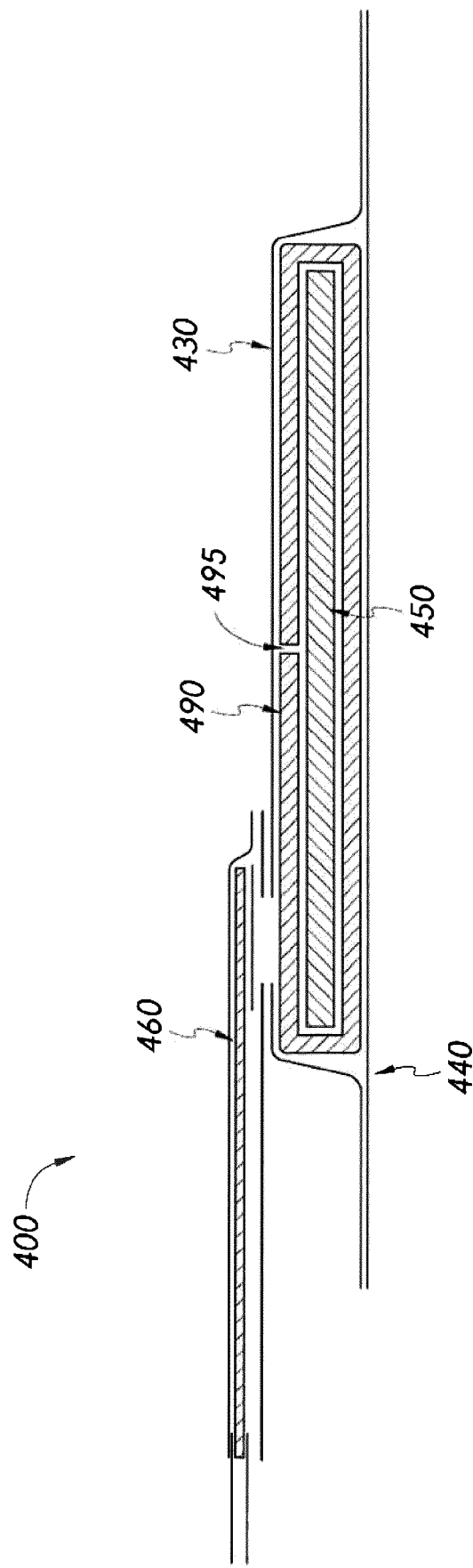
FIG. 7B illustrates a cross sectional view of an embodiment of a negative pressure wound treatment system employing a flexible fluidic connector and a wound dressing with a wrapped around spacer layer, the wound dressing capable of absorbing and storing wound exudate.
Figure 7C:
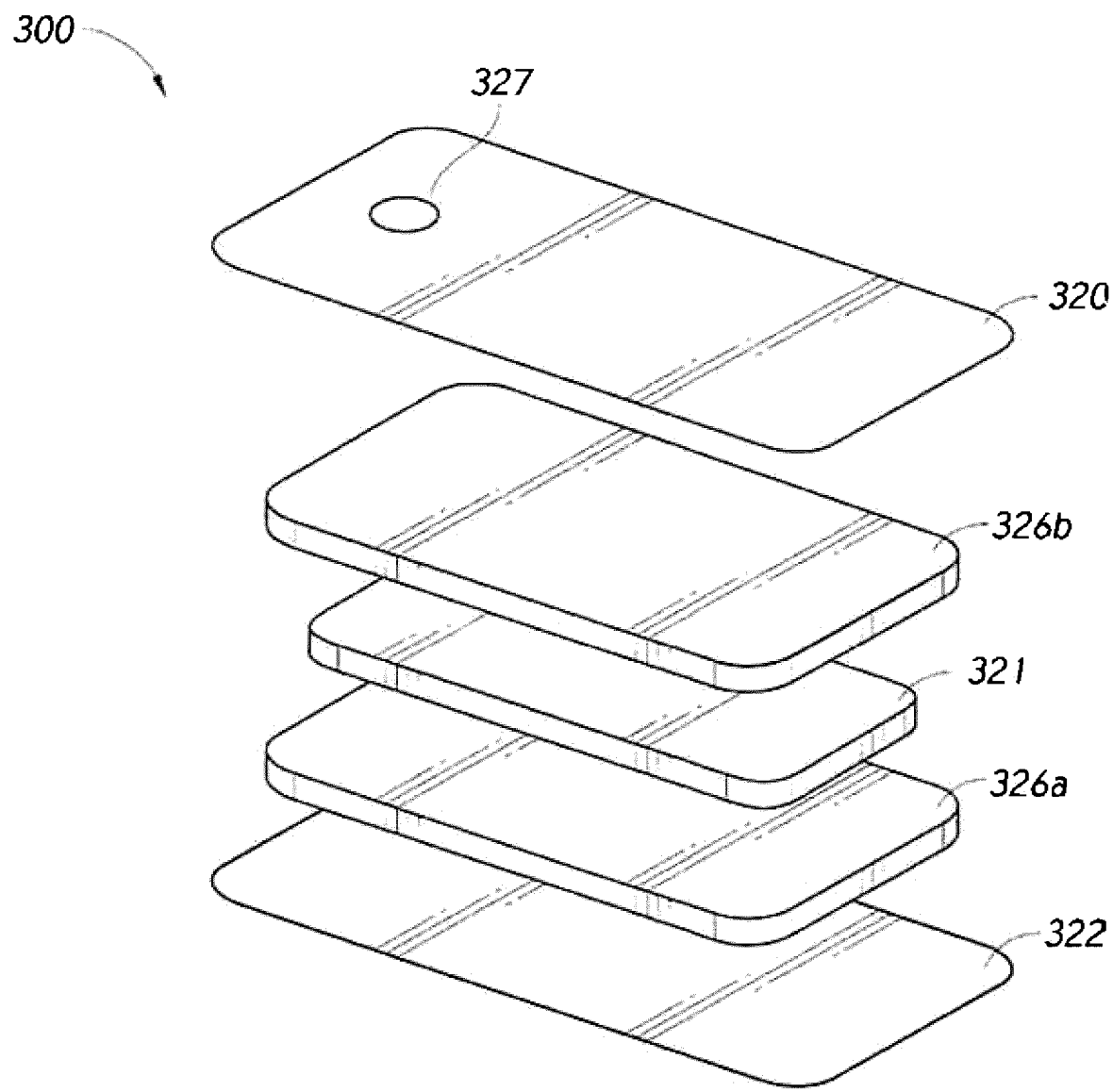
FIG. 7C illustrates an embodiment of a negative pressure wound treatment system employing a wound dressing capable of absorbing and storing wound exudate.

The cover layer 430, 320, which can be more clearly seen in FIG. 7B-7C, can be formed of substantially fluid impermeable material, such as film. The cover layer 430, 320 can be similar to the cover layer or backing layer described in FIGS. 4A-4D previously. The film may be transparent, such that from the top view of FIG. 7A, other layers underneath the cover layer are also visible. The cover layer can include an adhesive for securing the dressing to the surrounding skin or a wound contact layer. The dressing can utilize a wound contact layer 440, 322 and an absorbent layer 450, 321 within the dressing. The wound contact layer and the absorbent layer can be similar to the wound contact layer and absorbent layers described in FIGS. 4A-4D previously. The wound contact layer can be configured to be in contact with the wound. The wound contact layer can include an adhesive on the patient facing side for securing the dressing to the surround skin or on the top side for securing the wound contact layer 440, 322 to a cover layer 430, 320 or other layer of the dressing. In operation, in some embodiments the wound contact layer can be configured to provide unidirectional flow so as to facilitate removal of exudate from the wound while blocking or substantially preventing exudate from returning to the wound. Further, an absorbent layer (such as layer 450, 321) for absorbing and retaining exudate aspirated from the wound can be utilized. In some embodiments, the absorbent layer can include an absorbent material, for example, a superabsorbent material or other absorbent material known in the art. In some embodiments, the absorbent layer can include a shaped form of a superabsorber layer with recesses or compartments for the pump, electronics, and accompanying components. In some embodiments, the wound dressing can include multiple absorbent layers.

The absorbent material 450 as shown in FIG. 7A which may be a foam or non-woven natural or synthetic material and which may optionally include or be super-absorbent material, forms a reservoir for fluid, particularly liquid, removed from the wound site and draws those fluids towards a cover layer 430. The material of the absorbent layer can be similar to the absorbent material described with reference to FIGS. 4A-4D. The material of the absorbent layer also prevents liquid collected in the wound dressing from flowing in a sloshing manner. The absorbent layer 450 also helps distribute fluid throughout the layer via a wicking action so that fluid is drawn from the wound site and stored throughout the absorbent layer. This helps prevent agglomeration in areas of the absorbent layer.

In some embodiments, the absorbent layer is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing.

The wicking action also assists in delivering liquid downwards towards the wound bed when exudation slows or halts. This delivery process helps maintain the transmission layer or lower spacer layer and lower wound bed region in a moist state which helps prevent crusting within the dressing (which could lead to blockage) and helps maintain an environment optimized for wound healing.

In some embodiments, the absorbent layer may be an air-laid material. Heat fusible fibers may optionally be used to assist in holding the structure of the pad together. It will be appreciated that rather than using super-absorbing particles or in addition to such use, super-absorbing fibers may be utilized according to certain embodiments of the present invention. An example of a suitable material is the Product Chem-Posite™ 11 C available from Emerging Technologies Inc (ETi) in the USA.

Optionally, according to certain embodiments of the present invention, the absorbent layer may include synthetic stable fibers and/or bi-component stable fibers and/or natural stable fibers and/or super-absorbent fibers. Fibers in the absorbent layer may be secured together by latex bonding or thermal bonding or hydrogen bonding or a combination of any bonding technique or other securing mechanism. In some embodiments, the absorbent layer is formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer may comprise a layer of multiple fibers. Preferably, the fibers are strand-like and made from cellulose, polyester, viscose or the like. Preferably, dry absorbent particles are distributed throughout the absorbent layer ready for use. In some embodiments, the absorbent layer comprises a pad of cellulose fibers and a plurality of super absorbent particles. In additional embodiments, the absorbent layer is a non-woven layer of randomly orientated cellulose fibers.

Super-absorber particles/fibers may be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc.

Preferably, the particles of superabsorber are very hydrophilic and grab the fluid as it enters the dressing, swelling up on contact. An equilibrium is set up within the dressing core whereby moisture passes from the superabsorber into the dryer surrounding area and as it hits the top film the film switches and the fluid vapor starts to be transpired. A moisture gradient is established within the dressing to continually remove fluid from the wound bed and ensure the dressing does not become heavy with exudate.

The absorbent layer can include at least one through hole. The through hole can be located so as to underlie the suction port as described with reference to FIG. 4D. A single through hole can be used to produce an opening underlying the port 460 (not shown in FIG. 7B). It will be appreciated that multiple openings could alternatively be utilized. Additionally, should more than one port be utilized according to certain embodiments of the present invention one or multiple openings may be made in the super-absorbent layer in registration with each respective port. Although not essential to certain embodiments of the present invention the use of through holes in the super-absorbent layer provide a fluid flow pathway which is particularly unhindered and this is useful in certain circumstances.

Use of one or more through holes in the absorption layer also has the advantage that during use if the absorbent layer contains a gel forming material, such as superabsorber, that material as it expands to absorb liquid, does not form a barrier through which further liquid movement and fluid movement in general cannot pass. In this way each opening in the absorbent layer provides a fluid pathway between the lower transmission or spacer layer and the upper transmission or spacer layer to the wound facing surface of the filter and then onwards into the interior of the port.

These layers can be covered with one layer of a film or cover layer. The cover layer can include a filter that can be positioned over the absorbent layer, or a filter may be incorporated in the port 460 as described in International Application Publication No. WO 2013/175306 A2, U.S. Publication No. US2011/0282309, and U.S. Publication No. 2016/0339158 the entirety of which is hereby incorporated by reference. As shown in FIG. 7A gas impermeable, but moisture vapor permeable, cover layer 430 extends across the width of the wound dressing. The cover layer may be similar to the cover layer or backing layer described with reference to FIG. 4A-4D. The cover layer, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer and a wound site where a negative pressure can be established. The cover layer 430 is sealed to the wound contact layer 440 in a border region 410 around the circumference of the dressing, ensuring that no air is drawn in through the border area, for example via adhesive or welding techniques. The cover layer 430 protects the wound from external bacterial contamination (bacterial barrier) and allows liquid from wound exudates to be transferred through the layer and evaporated from the film outer surface. The cover layer 430 typically comprises two layers; a polyurethane film and an adhesive pattern spread onto the film. The polyurethane film is moisture vapor permeable and may be manufactured from a material that has an increased water transmission rate when wet.

The cover layer can include an aperture within the cover layer for providing fluid communication with a source of negative pressure or pump. The filter can be positioned in communication with the aperture in the wound cover. The aperture in the wound cover can be covered by a port 460. In some embodiments, the port 460 connects to a conduit for communication with a negative pressure source or pump. The port 460 can include a filter 420 provided to cover the aperture in the cover layer 430. In some embodiments, the filter 420 can be integral to the port 460. The filter 420 can include hydrophobic material to protect the pump and/or other components from liquid exudates. The filter 420 can block fluids while permitting gases to pass through. In some embodiments, the filter can be similar to the filter or filter system described in FIGS. 4A-4D previously. In some embodiments, the aperture in the cover layer 430 and the port 460 provide fluid communication between the wound dressing and a pump. In some embodiments, the pump, electronics, switch and battery can be positioned at a remote location from the dressing. In some embodiments, the pump, electronics, switch and battery can be positioned on top of the first cover layer and a second filter and second cover layer can be alternative or additionally used. For example, the second filter can be constructed from antibacterial and/or antimicrobial materials so that the pump can exhaust gases into the atmosphere. The second filter can also help to reduce noise produced by the pump.

Negative pressure can be lost at the wound bed when free absorbent capacity remains in the dressing. This can occur because some or all of the pores in the filter are blocked with liquid or particulates. In some embodiments, solutions are utilized to allow the full capacity of the dressing absorbent layer to be utilized whilst maintaining the air path between the source of negative pressure and the wound bed.

In dressing embodiments that utilize a cover layer directly over the absorbent layer the dressing can have a void underneath the filter which can fill with liquid, thus blocking the filter pores and preventing air flow to the wound bed. A spacer layer or transmission layer 490 can be used to provide a fluid flow path above the absorbent layer 450 preventing the blocking of the port 460. In some embodiments, the transmission layer 490 in the dressing can be provided above and below the absorbent layer. The transmission layer can be incompressible and maintain a path for fluid flow between the source of negative pressure and the wound bed, via the filter. In some embodiments, the transmission layer can encapsulate or wrap around the absorbent layer as shown in FIGS. 7A and 7B. The wrapped transmission layer can provide an uninterrupted length of transmission material from the filter 420 to the wound bed. The transmission layer can traverse the length of the top surface of the absorbent layer and wrap around at least one side of the absorbent layer and traverse the length of the bottom surface (wound facing surface) of the absorbent layer. In some embodiments, the transmission layer can wrap around two sides of the absorbent layer as shown in FIG. 7A.

In some embodiments, the transmission layer can be utilized to assist in distributing negative pressure over the wound site and facilitating transport of wound exudate and fluids into the wound dressing.

A lower portion of the transmission layer 490 of porous material can be located above the wound contact layer and below the absorbent layer and wrapped around the edges of the absorbent layer. As the transmission layer is wrapped around at least one edge of the absorbent layer, the transmission layer has an upper portion of the transmission layer that can be positioned between the cover layer and the absorbent layer. As used herein the edge of the absorbent layer or the dressing refers to the sides of the material that are substantially perpendicular to the wound surface and run along the height of the material.

In some embodiments, the transmission layer can be a porous layer. This spacer layer, or transmission layer, 490 allows transmission of fluid including liquid and gas away from a wound site into upper layers of the wound dressing as described with reference to FIG. 4D. In particular, the transmission layer 490 ensures that an open air channel can be maintained to communicate negative pressure over the wound area even when the absorbent layer has absorbed substantial amounts of exudates. The layer should remain open under the typical pressures that will be applied during negative pressure wound therapy as described previously, so that the whole wound site sees an equalized negative pressure. The transmission layer 490 may be formed of a material having a three dimensional structure. For example, a knitted or woven spacer fabric (for example Baltex 7970 weft knitted polyester) or a non-woven fabric could be used. Other materials, such as those described previously herein, could of course be utilized.

In some embodiments, the transmission layer can be formed from a vertically lapped material. In some embodiments, the transmission layer material can be one or more layers of a vertically lapped material as described previously herein and illustrated in FIGS. 1-3. In some embodiments, the vertically lapped material can include a first layer of an absorbing layer of material. In other embodiments, the vertically lapped material can include a first layer of a non-absorbing layer of material. In some embodiments, the first layer can optionally be temporarily or permanently attached to a second layer of material as described herein. The first layer can be constructed from at least one layer of non-woven textile fibers. The non-woven textile fibers can be folded into a plurality of folds to form a pleated structure. In some embodiments, a depth of the pleats of the pleated structure that has been slit can determine a thickness of the first layer of material. In some embodiments, the thickness of the wound dressing with vertically lapped material can be between 1 and 20 mm (or 2 to 10, or 3 to 7 mm). In some embodiments, the thickness of the vertically lapped material can be between 1 and 10 mm (or 2 to 7 mm). In some embodiments, the second layer of the vertically lapped material can be temporarily or permanently connected to the first layer of material. In some embodiments, the second layer can include a single or multi-layer construction. In some embodiments, the vertically lapped material can be formed from hydrophobic and/or hydrophilic fibers. The selection of fibers can vary the fluid handling properties of the vertically lapped material. The materials described with reference to FIGS. 7A-7C can apply to the materials described for these embodiments or elsewhere in the specification.

In some embodiments, the absorbent layer 405 can comprise a vertically lapped material with a first layer of an absorbing layer of material. The absorbing vertically lapped material can contain a super absorbent material or super absorbent fibers. In some embodiments, one or more layers of vertically lapped material may be used for both the absorbent layer 405 and the transmission layer 490. In such embodiments, the vertically lapped material can allow transmission of fluid including liquid and gas away from a wound site into upper layers of the wound dressing and can provide a reservoir for fluid, particularly liquid, removed from the wound site.

FIG. 7A illustrates a top view of an embodiment of a wound dressing with a transmission layer 490 wrapped around an absorbent layer 450. The wound dressing can be constructed with a wound contact layer 440 and a top film or cover layer 430 enclosing an absorbent layer 450. A hole or aperture in the top film 430 can be entirely covered by a port 460 which leads to a source of negative pressure. The port 460 can contain a filter 420 or can be positioned over the filter 420. The dressing absorbent layer 450 can comprise a superabsorbent material. The absorbent layer 450 can be surrounded fully or in part by a spacer fabric or transmission layer 490. The transmission layer 490 can be provided above and below the absorbent layer 450. In some embodiments, the transmission layer 490 can be wrapped around and cover two sides the absorbent layer 450. For example, in some embodiments, a length of the transmission layer 490 can be configured to provide a fluid flow that connects the wound contact surface 440 and the filter 420. As illustrated in FIG. 7A, the transmission layer can extend around the absorbent layer 450 running along the length of the bottom surface and top surface of the absorbent layer and wrapping around at least one side of the absorbent layer but not fully encapsulating the absorbent layer. In some embodiments, as shown in FIG. 7A, the transmission layer 490 extends to the periphery of the absorbent layer but does not extend over the ends of the width of the dressing. For example, as illustrated in FIG. 7A, the periphery of two sides of the absorbent layer 450 extend beyond the transmission layer 490 while the spacer layer extends over and wraps around the other two sides of the absorbent layer. In other embodiments, the transmission layer 490 fully encapsulates and all sides of the absorbent layer 450.

The port 460 can be positioned either above the top film or cover layer 430 at one end or in the center of the dressing. The port can be positioned over the aperture in the top film and can contain or be placed over the filter 420. As described herein, providing the transmission layer above and below and wrapped around at least one side of the absorbent layer can prevent the filter from becoming blocked with liquid or particulates, by allowing the distribution of fluid through the wrapped spacer layer until the full absorbent capacity of the dressing materials have been reached. This can increase the wear time of the wound dressing by prolonging delivery of negative pressure to the wound bed. In some embodiments, the dressing with the configuration of layers as described herein has demonstrated a longer delivery period of NPWT to the wound contact surface compared to wound dressing without the transmission layer between the absorbent layer and the cover layer and without the transmission layer wrapped around the absorbent layer.

FIG. 7B illustrates a cross-sectional view of the wound dressing with the transmission layer 490 wrapped around the absorbent layer 450. As shown in FIG. 7B, the wound contact layer 440 can be provided as the bottom layer of the dressing configured to contact the wound surface. The top film or cover layer 430 is provided as a top layer enclosing the transmission layer 490 and the absorbent layer 450 with the wound contact layer 440. The cover layer 430 can seal to the border region around the periphery of the wound contact layer 440, the skin of a patient, and/or the wound bed. The port 460 can be positioned above the cover layer 430 and over an aperture in the cover layer 430. As illustrated in FIG. 7B, the cross section of the wound dressing shows the transmission layer 490 surrounding the absorbent layer 450 so that the port 460 is in communication with the upper portion of the transmission material and the wound contact layer is in contact with the lower portion of the transmission material. The configuration of the transmission layer surrounding the absorbent material allows a fluid flow path from the wound bed or wound contact layer to the port without passing through the absorbent layer.

The transmission layer 490 can be wrapped around the absorbent layer 450 to disperse the vacuum throughout the dressing. In some embodiments, the transmission layer 490 can be manufactured as one flat piece of material that during assembly of the dressing is positioned on the bottom surface of the absorbent layer 450, wrapped around the ends of the absorbent layer 450, and the two ends of the spacer layer 490 are folded over the top surface of the absorbent layer 450 completely or partially covering the top surface of the absorbent layer 450. In such embodiments, the upper transmission layer 490 can have a break 495 in the transmission material where the two folded over ends of the transmission material 490 meet as shown in FIG. 7B. In alternative embodiments, the transmission layer 490 can be manufactured as one piece of transmission material that is pre-shaped to fit around the absorbent layer 450 and fully encapsulates the absorbent layer 450 with no break in the transmission material.

Providing the transmission layer between the port and the absorbent layer prevents fluid or exudate removed from the wound from blocking the port and/or filter within the port. There can be some free particles in the hole of the absorbent layer positioned below the filter. The loose free particles in the hole can gel and block the hole and/or filter area. Therefore, the upper transmission layer can keep the superabsorber particles clear from the filter and allow the dressing to fill completely. In some embodiments, the transmission layer wrapped around the absorbent layer allow the port to be located at any location with respect to gravity. The transmission layer positioned above the absorbent layer can eliminate the concerns of the fluid or exudate removed from the wound from blocking the port and/or filter within the port on the section of the absorbent layer that is filled first.

As shown in FIG. 7C, the wound dressing 300 can include a wound contact layer 322. The wound contact layer can be similar to the wound contact layer 322 described with reference to FIG. 4D. In some embodiments, the wound contact layer 322 can be a double-face coated (silicone-acrylic) perforated adhesive wound contact layer. A transmission layer 326a and absorbent layer 321 can be provided similar to the dressing described with reference to FIG. 4D but the transmission layer 326a over-borders the absorbent layer. The wound dressing 300 can include a second transmission layer 326b between the absorbent layer and the backing layer that over-borders the absorbent layer. The first and second transmission layers 326a and 326b can over-border the absorbent layer by 5 mm at the perimeter. This can be the reverse of the cut geometry in the dressings as described previously. In some embodiments, there is no through-hole or aperture in the absorbent layer 321 or second transmission layer 326b. In some embodiments, the hole in the absorbent layer could be disadvantageous because it could become filled with superabsorbent particles or other material and block the filter in the standard dressing. A backing layer 320 sits over the second transmission layer 326b and the backing layer can include an orifice 327 that allows connection of the fluidic connector to communicate negative pressure to the dressing.

In some embodiments, the first and second transmission layer 326a, 326b can include a 3D fabric. In some embodiments, the first and second transmission layers can include a vertically lapped material as described herein and illustrated in FIGS. 1-3. In some embodiments, the a vertically lapped material can include a first layer of an absorbing layer of material. In other embodiments, the vertically lapped material can include a first layer of a non-absorbing layer of material. In some embodiments, the first layer can optionally be temporarily or permanently attached to a second layer of material as described herein. The first layer can be constructed from at least one layer of non-woven textile fibers. The non-woven textile fibers can be folded into a plurality of folds to form a pleated structure. In some embodiments, a depth of the pleats of the pleated structure that has been slit can determine a thickness of the first layer of material. In some embodiments, the thickness of the wound dressing with vertically lapped material can be between 1 and 20 mm (or 2 to 10, or 3 to 7 mm). In some embodiments, the thickness of the vertically lapped material can be between 1 and 10 mm (or 2 to 7 mm). In some embodiments, the second layer of the vertically lapped material can be temporarily or permanently connected to the first layer of material. In some embodiments, the second layer can include a single or multi-layer construction. In some embodiments, the vertically lapped material can be formed from hydrophobic and/or hydrophilic fibers. The selection of fibers can vary the fluid handling properties of the vertically lapped material. In some embodiments, the first and second transmission layers 326a, 326b may be formed of a material having a three dimensional structure. For example, a knitted or woven spacer fabric (for example Baltex 7970 weft knitted polyester) or a non-woven fabric could be used as described previously. The first and second transmission layers 326a, 326b can allow transmission of fluid including liquid and gas away from a wound site into the layers of the wound dressing. In particular, the first and second transmission layers 326a, 326b preferably ensures that an open air channel can be maintained to communicate negative pressure over the wound area and throughout the wound dressing even when the absorbent layer has absorbed substantial amounts of exudates.

In some embodiments, the absorbent layer 450 can comprise a vertically lapped material with a first layer of an absorbing layer of material. The absorbing vertically lapped material can contain a super absorbent material or super absorbent fibers. In some embodiments, one or more layers of vertically lapped material may be used for both the absorbent layer 321 and one or more of the transmission layers 326a and 326b. In such embodiments, the vertically lapped material can allow transmission of fluid including liquid and gas away from a wound site into upper layers of the wound dressing and can provide a reservoir for fluid, particularly liquid, removed from the wound site.

Figure 8A:
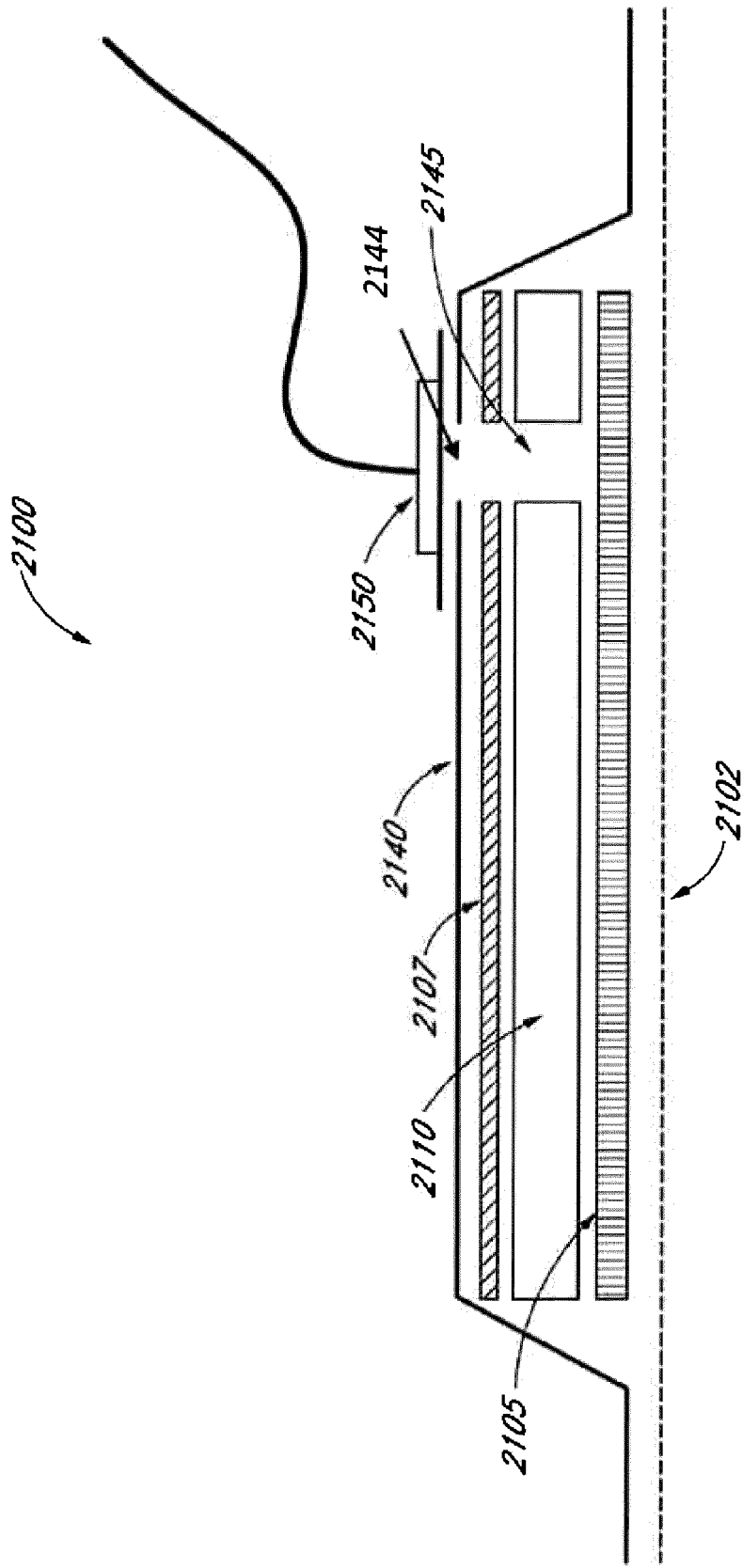
FIG. 8A illustrates another embodiment of a wound dressing in cross-section.

FIG. 8A illustrates a cross-section through a wound dressing 2100 similar to the wound dressing of FIGS. 4A-4D according to an embodiment of the disclosure. The wound dressing 2100, which can alternatively be any wound dressing embodiment disclosed herein including without limitation wound dressing 110 or any combination of features of any number of wound dressing embodiments disclosed herein, can be located over a wound site to be treated. The dressing 2100 may be placed to as to form a sealed cavity over the wound site. In a preferred embodiment, the dressing 2100 comprises a backing layer 2140 attached to a wound contact layer 2102, similar to the cover layer and wound contact layer described with reference to FIGS. 4A-4D. These two layers 2140, 2102 are preferably joined or sealed together so as to define an interior space or chamber. This interior space or chamber may comprise additional structures that may be adapted to distribute or transmit negative pressure, store wound exudate and other fluids removed from the wound, and other functions as described herein. Examples of such structures, described below, include a transmission layer 2105 and an absorbent layer 2110, similar to the transmission layer and absorbent layer described with reference to FIGS. 4A-4D.

A layer 2105 of porous material can be located above the wound contact layer 2102. This porous layer, or transmission layer, 2105 allows transmission of fluid including liquid and gas away from a wound site into upper layers of the wound dressing. In particular, the transmission layer 2105 preferably ensures that an open air channel can be maintained to communicate negative pressure over the wound area even when the absorbent layer has absorbed substantial amounts of exudates. The layer 2105 should preferably remain open under the typical pressures that will be applied during negative pressure wound therapy as described above, so that the whole wound site sees an equalized negative pressure.

In some embodiments, the transmission layer 2105 may be a vertically lapped material as described herein and illustrated in FIGS. 1-3. In some embodiments, the vertically lapped material can include a first layer of an absorbing layer of material and a second layer of material. In other embodiments, the vertically lapped material can include a first layer of a non-absorbing layer of material. In some embodiments, the first layer can optionally be temporarily or permanently attached to a second layer of material as described herein. The first layer can be constructed from at least one layer of non-woven textile fibers. The non-woven textile fibers can be folded into a plurality of folds to form a pleated structure. In some embodiments, a depth of the pleats of the pleated structure that has been slit can determine a thickness of the first layer of material. In some embodiments, the thickness of the wound dressing with vertically lapped material can be between 1 and 20 mm (or 2 to 10, or 3 to 7 mm). In some embodiments, the thickness of the vertically lapped material can be between 1 and 10 mm (or 2 to 7 mm). In some embodiments, the second layer of the vertically lapped material can be temporarily or permanently connected to the first layer of material. In some embodiments, the second layer can include a single or multi-layer construction. In some embodiments, the vertically lapped material can be formed from hydrophobic and/or hydrophilic fibers. The selection of fibers can vary the fluid handling properties of the vertically lapped material.

In some embodiments, the layer 2105 may be formed of a material having a three dimensional structure. For example, a knitted or woven spacer fabric (for example Baltex 7970 weft knitted polyester) or a non-woven fabric could be used.

A layer 2110 of absorbent material is provided above the transmission layer 2105. The absorbent material, which comprise a foam or non-woven natural or synthetic material, and which may optionally comprise a super-absorbent material, forms a reservoir for fluid, particularly liquid, removed from the wound site. In some embodiments, the layer 2100 may also aid in drawing fluids towards the backing layer 2140.

In some embodiments, the absorbent layer 2110 can comprise a vertically lapped material with a first layer of an absorbing layer of material. The absorbing vertically lapped material can contain a super absorbent material or super absorbent fibers. In some embodiments, one or more layers of vertically lapped material may be used for both the absorbent layer 2110 and one or more of the transmission layer 2105. In such embodiments, the vertically lapped material can allow transmission of fluid including liquid and gas away from a wound site into upper layers of the wound dressing and can provide a reservoir for fluid, particularly liquid, removed from the wound site.

With reference to FIG. 8A, a masking or obscuring layer 2107 can be positioned beneath at least a portion of the backing layer 2140. In some embodiments, the obscuring layer 2107 can have any of the same features, materials, or other details of any of the other embodiments of the obscuring layers disclosed herein, including but not limited to having any viewing windows or holes. Examples of wound dressings with obscuring layers and viewing windows are described in International Patent Publication WO2014/020440, the entirety of which is incorporated by reference in its entirety. Additionally, the obscuring layer 2107 can be positioned adjacent to the backing layer, or can be positioned adjacent to any other dressing layer desired. In some embodiments, the obscuring layer 2107 can be adhered to or integrally formed with the backing layer. Preferably, the obscuring layer 2107 is configured to have approximately the same size and shape as the absorbent layer 2110 so as to overlay it. As such, in these embodiments the obscuring layer 2107 will be of a smaller area than the backing layer 2140.

The material of the absorbent layer 2110 may also prevent liquid collected in the wound dressing 2100 from flowing freely within the dressing, and preferably acts so as to contain any liquid collected within the absorbent layer 2110. The absorbent layer 2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 2110 may typically be manufactured from ALLEVYN™ foam, Freudenberg 114-224-4 and/or Chem-Posite™11C-450. In some embodiments, the absorbent layer 2110 may comprise a composite comprising superabsorbent powder, fibrous material such as cellulose, and bonding fibers. In a preferred embodiment, the composite is an airlaid, thermally-bonded composite.

An orifice 2144 is preferably provided in the backing layer 2140 to allow a negative pressure to be applied to the dressing 2100. A suction port 2150 is preferably attached or sealed to the top of the backing layer 2140 over an orifice 2144 made into the dressing 2100, and communicates negative pressure through the orifice 2144. A length of tubing may be coupled at a first end to the suction port 2150 and at a second end to a pump unit (not shown) to allow fluids to be pumped out of the dressing. The port may be adhered and sealed to the backing layer 2140 using an adhesive such as an acrylic, cyanoacrylate, epoxy, UV curable or hot melt adhesive. The port 2150 is formed from a soft polymer, for example a polyethylene, a polyvinyl chloride, a silicone or polyurethane having a hardness of 30 to 90 on the Shore A scale. In some embodiments, the port 2150 may be made from a soft or conformable material.

Preferably the absorbent layer 2110 and the obscuring layer 2107 include at least one through hole 2145 located so as to underlie the port 2150. Of course, the respective holes through these various layers 2107, 2140, and 2110 may be of different sizes with respect to each other. As illustrated in FIG. 8A a single through hole can be used to produce an opening underlying the port 2150. It will be appreciated that multiple openings could alternatively be utilized. Additionally should more than one port be utilized according to certain embodiments of the present disclosure one or multiple openings may be made in the absorbent layer and the obscuring layer in registration with each respective port. Although not essential to certain embodiments of the present disclosure the use of through holes in the super-absorbent layer may provide a fluid flow pathway which remains unblocked in particular when the absorbent layer 2110 is near saturation.

The aperture or through-hole 2144 is preferably provided in the absorbent layer 2110 and the obscuring layer 2107 beneath the orifice 2144 such that the orifice is connected directly to the transmission layer 2105. This allows the negative pressure applied to the port 2150 to be communicated to the transmission layer 2105 without passing through the absorbent layer 2110. This ensures that the negative pressure applied to the wound site is not inhibited by the absorbent layer as it absorbs wound exudates. In other embodiments, no aperture may be provided in the absorbent layer 2110 and/or the obscuring layer 2107, or alternatively a plurality of apertures underlying the orifice 2144 may be provided.

The backing layer 2140 is preferably gas impermeable, but moisture vapor permeable, and can extend across the width of the wound dressing 2100. The backing layer 2140, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 2140 and a wound site where a negative pressure can be established. The backing layer 2140 is preferably sealed to the wound contact layer 2102 in a border region 2200 around the circumference of the dressing, ensuring that no air is drawn in through the border area, for example via adhesive or welding techniques. The backing layer 2140 protects the wound from external bacterial contamination (bacterial barrier) and allows liquid from wound exudates to be transferred through the layer and evaporated from the film outer surface. The backing layer 2140 preferably comprises two layers; a polyurethane film and an adhesive pattern spread onto the film. The polyurethane film is preferably moisture vapor permeable and may be manufactured from a material that has an increased water transmission rate when wet.

In some embodiments, the absorbent layer 2110 may be of a greater area than the transmission layer 2105, such that the absorbent layer overlaps the edges of the transmission layer 2105, thereby ensuring that the transmission layer does not contact the backing layer 2140. This provides an outer channel 2115 of the absorbent layer 2110 that is in direct contact with the wound contact layer 2102, which aids more rapid absorption of exudates to the absorbent layer. Furthermore, this outer channel 2115 ensures that no liquid is able to pool around the circumference of the wound cavity, which may otherwise seep through the seal around the perimeter of the dressing leading to the formation of leaks.

Figure 8B:
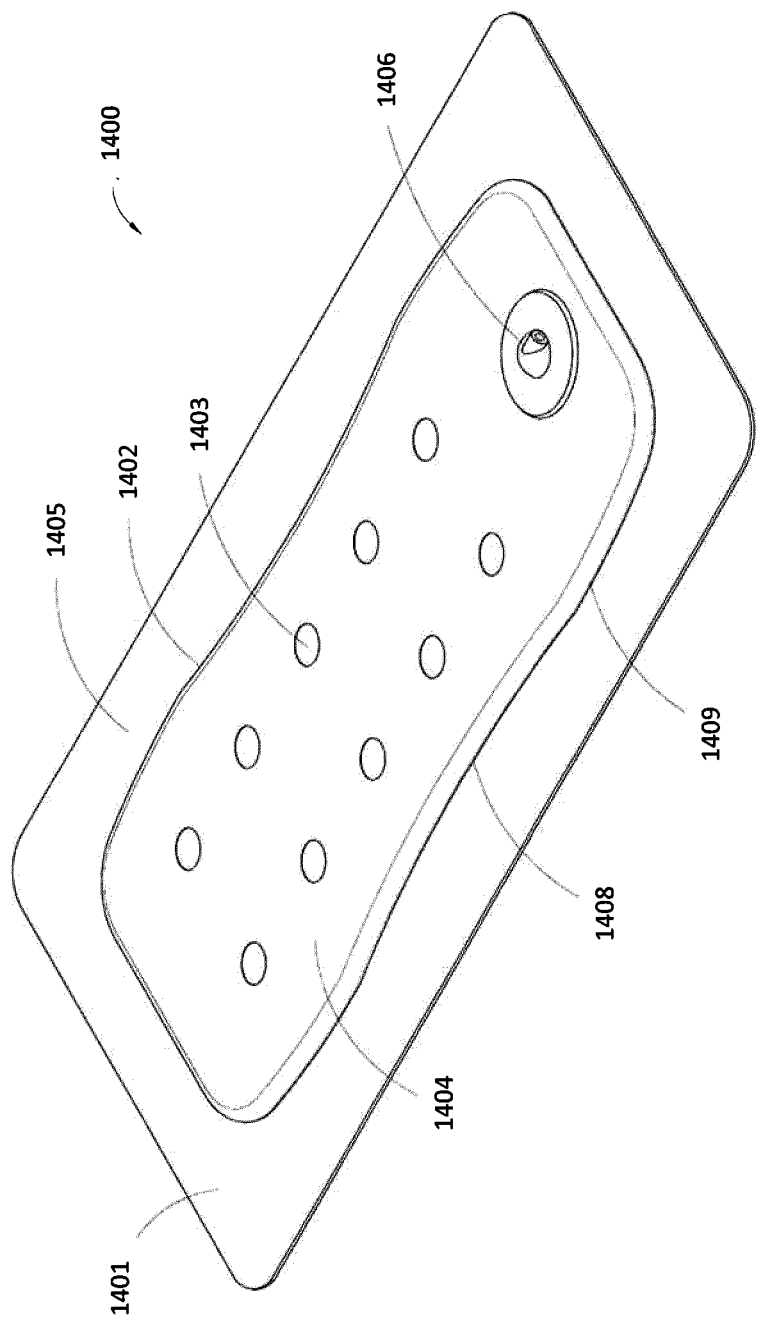
FIG. 8B illustrates a perspective view of an embodiment of a wound dressing including an obscuring layer and viewing windows.

FIG. 8B illustrates a view of an embodiment of a wound dressing with a waisted portion, an obscuring layer, and viewing windows. FIG. 8B illustrates a perspective view of an embodiment of a wound dressing 1400. The wound dressing 1400 preferably comprises a port 1406. The port 1406 is preferably configured to be in fluid communication with a pump, and may include a tube or conduit pre-attached to the port. Alternatively, negative pressure can be supplied to the wound dressing through other suitable fluidic connectors, including but not limited to the fluidic connectors of the type described below in FIGS. 4A-4D.

The wound dressing 1400 can be constructed similar to the embodiments of FIG. 8A above, and may comprise an absorbent material 1402 underneath or within a backing layer 1405. Optionally, a wound contact layer and a transmission layer may also be provided as part of the wound dressing 1400 as described above with reference to FIG. 8A. The absorbent material 1402 can contain a narrowed central or waisted portion 1408 to increase flexibility and conformability of the wound dressing to the skin surface. The backing layer 1405 may have a border region 1401 that extends beyond the periphery of the absorbent material 1402. The backing layer 1405 may be a translucent or transparent backing layer, such that the border region 1401 created from the backing layer 1405 can be translucent or transparent. The area of the border region 1401 of the backing layer 405 can be approximately equal around the perimeter of the entire dressing with the exception of the narrowed central portion, where the area of the border region is larger. One will recognize that the size of the border region 1401 will depend on the full dimensions of the dressing and any other design choices.

As illustrated in FIG. 8B, provided at least at the top of or over the absorbent layer 1402 and under the backing layer 1405 may be an obscuring layer 1404 that optionally has one or more viewing windows 1403. The obscuring layer 1404 may partially or completely obscure contents (such as fluids)

contained within the wound dressing 1400 and/or the absorbent material (i.e., within the absorbent material 1402 or under the backing layer 1405). The obscuring layer may be a colored portion of the absorbent material, or may be a separate layer that covers the absorbent material. In some embodiments, the absorbent material 1402 may be hidden (partially or completely), colored, or tinted, via the obscuring layer 1404, so as to provide cosmetic and/or aesthetic enhancements, in a similar manner to what is described above. The obscuring layer is preferably provided between the topmost backing layer 1405 and the absorbent material 1402, although other configurations are possible. The cross-sectional view in FIG. 8A illustrates this arrangement with respect to the masking or obscuring layer 2107. Other layers and other wound dressing components can be incorporated into the dressing as herein described.

The obscuring layer 1404 can be positioned at least partially over the absorbent material 1402. In some embodiments, the obscuring layer 1404 can be positioned adjacent to the backing layer, or can be positioned adjacent to any other dressing layer desired. In some embodiments, the obscuring layer 1404 can be adhered to or integrally formed with the backing layer and/or the absorbent material.

As illustrated in FIG. 8B, the obscuring layer 1404 can have substantially the same perimeter shape and size as the absorbent material 1402. The obscuring layer 1404 and absorbent material 1402 can be of equal size so that the entirety of the absorbent material 1402 can be obscured by the obscuring layer 1404. The obscuring layer 1404 may allow for obscuring of wound exudate, blood, or other matter released from a wound. Further, the obscuring layer 1404 can be completely or partially opaque having cut-out viewing windows or perforations.

In some embodiments, the obscuring layer 1404 can help to reduce the unsightly appearance of a dressing during use, by using materials that impart partial obscuring or masking of the dressing surface. The obscuring layer 1404 in one embodiment only partially obscures the dressing, to allow clinicians to access the information they require by observing the spread of exudate across the dressing surface. The partial masking nature of this embodiment of the obscuring layer enables a skilled clinician to perceive a different color caused by exudate, blood, by-products etc. in the dressing allowing for a visual assessment and monitoring of the extent of spread across the dressing. However, since the change in color of the dressing from its clean state to a state containing exudate is only a slight change, the patient is unlikely to notice any aesthetic difference. Reducing or eliminating a visual indicator of wound exudate from a patient's wound is likely to have a positive effect on their health, reducing stress for example.

In some embodiments, the obscuring layer can be formed from a non-woven fabric (for example, polypropylene), and may be thermally bonded using a diamond pattern with 19% bond area. In various embodiments, the obscuring layer can be hydrophobic or hydrophilic. Depending on the application, in some embodiments, a hydrophilic obscuring layer may provide added moisture vapor permeability. In some embodiments, however, hydrophobic obscuring layers may still provide sufficient moisture vapor permeability (i.e., through appropriate material selection, thickness of the obscuring layer), while also permitting better retention of dye or color in the obscuring layer. As such, dye or color may be trapped beneath the obscuring layer. In some embodiments, this may permit the obscuring layer to be colored in lighter colors or in white. In the preferred embodiment, the obscuring layer is hydrophobic. In some embodiments, the obscuring layer material can be sterilizable using ethylene oxide. Other embodiments may be sterilized using gamma irradiation, an electron beam, steam or other alternative sterilization methods. Additionally, in various embodiments the obscuring layer can colored or pigmented, e.g., in medical blue. The obscuring layer may also be constructed from multiple layers, including a colored layer laminated or fused to a stronger uncolored layer. Preferably, the obscuring layer is odorless and exhibits minimal shedding of fibers.

The absorbent layer 1402, itself may be colored or tinted in some embodiments, however, so that an obscuring layer is not necessary. The dressing may optionally include a means of partially obscuring the top surface. This could also be achieved using a textile (knitted, woven, or non-woven) layer without openings, provided it still enables fluid evaporation from the absorbent structure. It could also be achieved by printing an obscuring pattern on the top film, or on the top surface of the uppermost pad component, using an appropriate ink or colored pad component (yarn, thread, coating) respectively. Another way of achieving this would be to have a completely opaque top surface, which could be temporarily opened by the clinician for inspection of the dressing state (for example through a window), and closed again without compromising the environment of the wound. Additionally, FIG. 8B illustrates an embodiment of the wound dressing including one or more viewing windows 1403. The one or more viewing windows 1403 preferably extend through the obscuring layer 1404. These viewing windows 1403 may allow visualization by a clinician or patient of the wound exudate in the absorbent material below the obscuring layer. FIG. 8B illustrates an array of dots (e.g., in one or more parallel rows) that can serve as viewing windows 1403 in the obscuring layer 1404 of the wound dressing. In a preferred embodiment, two or more viewing windows 1403 may be parallel with one or more sides of the dressing 1400. In some embodiments, the one or more viewing windows may measure between 0.1 mm and 20 mm, preferably 0.4 mm to 10 mm, and even more preferably, 1 mm to 4 mm. The viewing windows 1403 may be cut through the obscuring layer 1404 or may be part of an uncolored area of the obscuring layer 1404 and therefore may allow visualization of the absorbent material 1402. The one or more viewing windows 1403 can be arranged in a repeating pattern across the obscuring layer 1404 or can be arranged at random across the obscuring layer. Additionally, the one or more viewing windows can be a circular shape or dots. Preferably, the one or more viewing windows 1403 are configured so as to permit not only the degree of saturation, but also the progression or spread of fluid toward the fluid port 1406, as in some embodiments, dressing performance may be adversely affected when the level of fluid has saturated the fluid proximate the port 1406. In some embodiments, a "starburst" array of viewing windows 1403 emanating around the port 1406 may be suitable to show this progression, although of course other configurations are possible. In some embodiments, the viewing windows 1403 correspond to the area of the absorbent material 1402 that is not covered by the obscuring layer 1404. As such, the absorbent material 1402 is directly adjacent the backing layer 1405 in this area. Since the obscuring layer 1404 acts as a partial obscuring layer, the viewing windows 1403 may be used by a clinician or other trained user to assess the spread of wound exudate throughout the dressing. In some embodiments, the viewing windows 1403 can comprise an array of dots or crescent shaped cut-outs. For example, an array of dots as viewing windows 1403 are illustrated in FIG. 8B in which the array of dots are arranged in an 5×2 array. Additionally, in some embodiments, the dot pattern can be distributed evenly throughout the obscuring layer and across the entire or substantially the entire surface of the obscuring layer. In some embodiments, the viewing windows 1403 may be distributed randomly throughout the obscuring layer. Preferably, the area of the obscuring layer 1404 uncovered by the one or more viewing windows 1403 is balanced to as to minimize the appearance of exudate while permitting the inspection of the dressing 1400 and/or absorbent material 1402. In some embodiments, the area exposed by the one or more viewing windows 1403 does not exceed 20% of the area of the obscuring layer 1404, preferably 10%, and even more preferably 5%.

The viewing windows 1403 may take several configurations. In some embodiments, the viewing windows 1403 may comprise an array of regularly spaced uncolored dots (holes) made into the obscuring layer 1404. While the dots illustrated here are in a particular pattern, the dots may be arranged in different configurations, or at random. The viewing windows 1403 are preferably configured so as to permit a patient or caregiver to ascertain the status of the absorbent layer, in particular to determine its saturation level, as well as the color of the exudate (e.g., whether excessive blood is present). By having one or more viewing windows, the status of the absorbent layer can be determined in an unobtrusive manner that is not aesthetically unpleasing to a patient. Because a large portion of the absorbent layer may be obscured, the total amount of exudate may therefore be hidden. As such, the status and saturation level of the absorbent layer 1402 may therefore present a more discreet external appearance so as to reduce patient embarrassment and visibility and thereby enhance patient comfort. In some configurations, the one or more viewing windows 1403 may be used to provide a numerical assessment of the degree of saturation of the dressing 1400. This may be done electronically (e.g., via a digital photograph assessment), or manually. For example, the degree of saturation may be monitored by counting the number of viewing windows 1403 which may be obscured or tinted by exudate or other wound fluids.

In some embodiments, the absorbent layer 1402 or the obscuring layer 1404, in particular the colored portion of the absorbent layer, may comprise (or be colored because of) the presence of an auxiliary compound. The auxiliary compound may in some embodiments be activated charcoal, which can act to absorb odors. The use of antimicrobial, antifungal, anti-inflammatory, and other such therapeutic compounds is also possible. In some embodiments, the color may change as a function of time (e.g., to indicate when the dressing needs to be changed), if the dressing is saturated, or if the dressing has absorbed a certain amount of a harmful substance (e.g., to indicate the presence of infectious agents). In some embodiments, the one or more viewing windows 1403 may be monitored electronically, and may be used in conjunction with a computer program or system to alert a patient or physician to the saturation level of the dressing 1400.

In one embodiment the disclosed technology relates to a wound dressing comprising a vertically lapped material comprising:
 a first layer of an absorbing layer of material, and
 a second layer of material,
 wherein the first layer being constructed from at least one layer of non-woven textile fibers, the non-woven textile fibers being folded into a plurality of folds to form a pleated structure; and
 the second layer of material is temporarily or permanently connected to the first layer of material, wherein the vertically lapped material has been slitted.

In one embodiment the disclosed technology relates to a wound dressing comprising a vertically lapped material comprising:
 a first layer of an absorbing layer of material, and
 a second layer of material,
 wherein the first layer being constructed from at least one layer of non-woven textile fibers, the non-woven textile fibers being folded into a plurality of folds to form a pleated structure; and
 the second layer of material is temporarily or permanently connected to the first layer of material, wherein the wound dressing may comprise two or more layers of the absorbing layer of material vertically lapped material stacked one on top of the other, wherein the two or more layers have the same or different densities or composition.

In one embodiment the disclosed technology relates to the use of a vertically lapped material as an absorbing layer of a wound dressing wherein the absorbing layer removes exudate from the wound, and the wound dressing comprises a vertically lapped material comprising:
 a first layer of an absorbing layer of material, and
 a second layer of material,
 wherein the first layer being constructed from at least one layer of non-woven textile fibers, the non-woven textile fibers being folded into a plurality of folds to form a pleated structure; and
 the second layer of material is temporarily or permanently connected to the first layer of material.

In one embodiment the disclosed technology relates to a wound dressing comprising a vertically lapped material comprising:
 a first layer of an absorbing layer of material, and
 a second layer of material,
 wherein the first layer being constructed from at least one layer of non-woven textile fibers, the non-woven textile fibers being folded into a plurality of folds to form a pleated structure; and
 the second layer of material is temporarily or permanently connected to the first layer of material, wherein the absorbing layer of material is a blend of 5 to 95% thermoplastic polymer, and 5 to 95 wt % of a cellulose or derivative thereof.

Each of the documents referred to above is incorporated herein by reference.

Except in the Examples, or where otherwise explicitly indicated, all numerical quantities in this description specifying amounts of materials, processing conditions and the like, are to be understood as modified by the word "about."

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:
1. A wound dressing comprising a vertically lapped material comprising:
 a first layer of an absorbing material, and
 a second layer of material,
 wherein the first layer is constructed from at least one layer of non-woven textile fibers, the at least one layer of non-woven textile fibers being folded into a plurality of folds to form a pleated structure comprising a plurality of bottom folds on a first wound facing side and a plurality of top folds on a second side opposite the first side, wherein the pleated structure is slitted to remove at least one of the plurality of top folds or the plurality of bottom folds of the first layer to determine a thickness of the first layer; and the second layer of material is temporarily or permanently connected to the first layer of material.

2. The wound dressing of claim 1, wherein the first layer comprises slits extending through a thickness of the first layer.

3. The wound dressing of claim 1, wherein second layer comprises a foam or a dressing fixative.

4. The wound dressing of claim 3, wherein the foam is a polyurethane foam.

5. The wound dressing of claim 3, wherein the dressing fixative includes bandages, tape, gauze, or backing layer.

6. The wound dressing of claim 1, wherein the wound dressing further comprises a wound contact layer.

7. A method of providing negative pressure wound therapy to a wound, the method comprising:
placing the wound dressing of claim 1 over a wound;
forming a fluid flow path between the wound dressing and a negative pressure source; and
operating the negative pressure source to provide negative pressure to the wound.

8. A method of operating a negative pressure wound system, the method comprising:
operating a negative pressure source fluidically connected to the wound dressing of claim 1, the wound dressing configured to be positioned over a wound.

9. A non-negative pressure method of providing wound therapy to a wound, the method comprising: placing the wound dressing of claim 1 over a wound; and
securing the wound dressing with a dressing fixative.

10. A method of manufacturing a wound dressing, the method comprising:
(i) forming a vertically lapped material comprising an absorbing material, and
(ii) attaching the absorbing material from step (i) to a second layer of material,
wherein the absorbing material is constructed from at least one layer of non-woven textile fibers, the at least one layer of non-woven textile fibers being folded into a plurality of folds to form a pleated structure and the pleated structure is subsequently slitted to determine a thickness of the absorbing material; and
the second layer of material is temporarily or permanently connected to the absorbing material, and
wherein the thickness of the wound dressing is between 1 and 20 mm.

11. The method of claim 10, wherein a depth of the pleats of the pleated structure that has been slit determines the thickness of the absorbing material.

12. The method of claim 10, wherein the absorbing material comprises slits extending through a thickness of the absorbing material.

13. The method of claim 10, wherein the pleated structure of the absorbing material comprises a plurality of bottom folds on a first wound facing side and a plurality of top folds on a second side opposite the first side, wherein the pleated structure is slitted to remove at least one of the plurality of top folds or the plurality of bottom folds of the absorbing material to determine a thickness of the absorbing material.

14. A wound dressing comprising:
at least one layer of a vertically lapped material, and
a cover layer configured to cover and form a seal over a wound; and
wherein the at least one layer of the vertically lapped material is constructed from at least one layer of non-woven textile fibers, the at least one layer of non-woven textile fibers being folded into a plurality of folds to form a pleated structure comprising a plurality of bottom folds on a first wound facing side and a plurality of top folds on a second side opposite the first side, wherein the pleated structure is slitted to remove at least one of the plurality of top folds or the plurality of bottom folds of the at least one layer of the vertically lapped material to determine a thickness of the at least one layer of the vertically lapped material.

15. The wound dressing of claim 14, wherein the wound dressing further comprises a wound contact layer.

16. The wound dressing of claim 14, wherein the at least one layer of the vertically lapped material comprises an absorbent material configured to provide a reservoir for fluid removed from the wound.

17. The wound dressing of claim 16, wherein the wound dressing further comprises a transmission layer configured to allow transmission of fluid away from a wound site into upper layers of the wound dressing.

18. The wound dressing of claim 14, wherein the at least one layer of the vertically lapped material comprises a transmission layer configured to allow transmission of fluid away from a wound site into upper layers of the wound dressing.

19. The wound dressing of claim 18, wherein the wound dressing further comprises an absorbent layer.

20. The wound dressing of claim 14, wherein the wound dressing further comprises an obscuring layer.

21. The wound dressing of claim 20, wherein the obscuring layer comprises one or more viewing windows.

22. The wound dressing of claim 14, wherein the at least one layer of the vertically lapped material comprises an upper portion and a lower portion, wherein the upper portion and lower portion of the vertically lapped material are configured to be in fluid communication, the upper portion and lower portion are configured to allow transmission of fluid away from a wound site; and the wound dressing further comprises an absorbent layer, wherein the at least one layer of the vertically lapped material is configured to be wrapped around at least one edge of the absorbent layer with the upper portion of the vertically lapped material being above the absorbent layer and the lower portion of the vertically lapped material being below the absorbent layer.

23. The wound dressing of claim 14, wherein the at least one layer of the vertically lapped material comprises a first and second vertically lapped material and the wound dressing further comprises an absorbent layer;
wherein the first vertically lapped material is positioned below the absorbent layer, the first vertically lapped material having a perimeter larger than a perimeter of the absorbent layer; and
wherein the second vertically lapped material is positioned above the absorbent layer, the second vertically lapped material having a perimeter larger than the perimeter of the absorbent layer.

24. The wound dressing of claim 14, in combination with a negative pressure source.

25. The wound dressing of claim 24, wherein the negative pressure source is positioned within the wound dressing.

26. The wound dressing of claim 25, wherein the negative pressure source is positioned within or adjacent to a transmission layer.

27. The wound dressing of claim 25, wherein the negative pressure source is positioned within or adjacent to an absorbent layer.

28. The wound dressing of claim 24, further comprising a suction adapter positioned over an opening in the cover layer to provide negative pressure to the wound dressing.

29. The wound dressing of claim 28, wherein the suction adapter comprises an elongate bridge containing a vertically lapped material.

30. The wound dressing of claim 14, wherein the at least one layer of the vertically lapped material comprises slits extending through a thickness of the at least one layer of the vertically lapped material.

\* \* \* \* \*